United States Patent
Thomas et al.

(10) Patent No.: US 11,613,514 B2
(45) Date of Patent: Mar. 28, 2023

(54) CRYSTAL FORMS AND METHODS OF SYNTHESIS OF (2R, 6R)-HYDROXYNORKETAMINE AND (2S, 6S)-HYDROXYNORKETAMINE

(71) Applicants: THE UNITED STATES OF AMERICA, AS REPRESENTED BY THE SECRETARY, DEPARTMENT OF HEALTH AND HUMAN SERVICES, Bethesda, MD (US); University of Maryland, Baltimore, Baltimore, MD (US)

(72) Inventors: Craig Thomas, Gaithersburg, MD (US); Carlos Zarate, Germantown, MD (US); Ruin Moaddel, Bel Air, MD (US); Todd Gould, Elkridge, MD (US); Panos Zanos, Baltimore, MD (US); Patrick Morris, Columbia, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 17/155,162

(22) Filed: Jan. 22, 2021

(65) Prior Publication Data
US 2021/0139411 A1 May 13, 2021

Related U.S. Application Data

(62) Division of application No. 16/088,371, filed as application No. PCT/US2017/024241 on Mar. 27, 2017, now Pat. No. 10,919,842.

(Continued)

(51) Int. Cl.
C07C 225/20 (2006.01)
C07C 221/00 (2006.01)
C07C 269/06 (2006.01)

(52) U.S. Cl.
CPC .......... *C07C 225/20* (2013.01); *C07C 221/00* (2013.01); *C07C 269/06* (2013.01);
(Continued)

(58) Field of Classification Search
None
See application file for complete search history.

(56) References Cited

U.S. PATENT DOCUMENTS

| 9,096,537 B1 | 8/2015 | Kandula |
| 9,650,352 B2 * | 5/2017 | Wainer ............... C07D 295/155 |
| 2015/0259277 A1 * | 9/2015 | Sleigh ..................... A61P 29/00 514/538 |

FOREIGN PATENT DOCUMENTS

| AU | 8722075 | * 12/1974 | ............. C07B 57/00 |
| CN | 104837810 | 8/2015 |

(Continued)

OTHER PUBLICATIONS

AU-8722075 Derwent Abstract, Dec. 1975 1 page.*
(Continued)

*Primary Examiner* — Clinton A Brooks
(74) *Attorney, Agent, or Firm* — Cantor Colburn LLP

(57) ABSTRACT

The disclosure provides a method for synthesizing free base forms of (2R,6R)-hydroxynorketamine (HNK) and (2S,6S)-hydroxynorketamine. In an embodiment synthesis of (2R, 6R)-hydroxynorketamine (HNK) includes preparation of (R)-norketamine via chiral resolution from racemic norketamine via a chiral resolution with L-pyroglutamic acid. The disclosure also provided crystal forms of the corresponding (Continued)

(2R,6R)-hydroxynorketamine (HNK) and (2S,6S)-hydroxynorketamine hydrochloride salts.

15 Claims, 4 Drawing Sheets

Related U.S. Application Data

(60) Provisional application No. 62/313,309, filed on Mar. 25, 2016.

(52) U.S. Cl.
CPC ...... *C07B 2200/13* (2013.01); *C07C 2601/14* (2017.05); *C07C 2601/16* (2017.05)

(56) References Cited

FOREIGN PATENT DOCUMENTS

| CN | 109475514 A | 3/2019 |
| EP | 3505509 A1 | 7/2019 |
| WO | 2009131794 A1 | 10/2009 |
| WO | 2013056229 A1 | 4/2013 |
| WO | 2014020155 A1 | 2/2014 |

OTHER PUBLICATIONS

Leung, et al., "Comparative Pharmacology in the Rat of Ketamine and Its Two Principal Metabolites, Norketamine and (Z)-6-Hydroxynorketamine", J. Med. Chem. 1986, 29, pp. 2396-2399.

"Characterization of Crystalline and Partially Crystalline Solids by X-Ray Powder Diffraction (XRPD)", United States Pharmacopeial Forum, vol. 35, No. 3, 2005, 11 pages.

Harry G. Brittain, "Polymorphism in Pharaceutical Solids" Second Edition, Drugs and the Pharmaceutical Sciences, vol. 192, 2016, 241 pages.

Hilfiker, et al., "Relevance of Solid-state Properties ofr Pharmaceutical products", Jan. 1, 2006, pp. 1-19, XP002525043, ISBN: 978-3-527-31146-0.

Hong et al., "Stereochemical Studies of Demethylated Ketamine Enantiomers", Journal of Pharmaceutical Sciences, vol. 71, No. 8, Jul. 13, 1981, pp. 912-914.

International Preliminary Report on Patentability issued in Application No. PCT/US2017/024241 dated Sep. 25, 2018, 9 pages.

International Search Report dated Jul. 19, 2017; International Application No. PCT/US2017/024241; International Filing Date Mar. 27, 2017; (8 pages).

Written Opinion dated Jul. 19, 2017; International Application No. PCT/US2017/024241; International Filing Date Mar. 27, 2017 (10 pages).

\* cited by examiner

CRYSTAL FORMS AND METHODS OF SYNTHESIS OF (2R, 6R)-HYDROXYNORKETAMINE AND (2S, 6S)-HYDROXYNORKETAMINE

CROSS REFERENCE TO RELATED APPLICATION

This Application is a Divisional of U.S. application Ser. No. 16/088,371 filed Sep. 25, 2018, which is a U.S. National Stage Application of PCT/US2017/024241, filed Mar. 27, 2017, which claims priority to U.S. Provisional Application No. 62/313,309 filed Mar. 25, 2016, all of which are incorporated by reference in their entireties.

STATEMENT OF GOVERNMENT SUPPORT

This invention was made with government support under Grant Numbers MH107615 and NH099345 awarded by the National Institutes of Health. The United States government has certain rights in the invention.

BACKGROUND

Ketamine, a drug currently used in human anesthesia and veterinary medicine, has been shown in clinical studies to be effective in the treatment of several conditions, including pain, treatment-resistant bipolar depression, major depressive disorder, and other depression and anxiety-related disorders.

However, the routine use of the drug is hindered by unwanted central nervous system (CNS) effects. Approximately 30% of patients do not respond to ketamine treatment. Additionally, ketamine treatment is associated with serious side effects due to the drug's anesthetic properties and abuse potential.

Ketamine analogs have potential advantages over standard antidepressants, as the time to efficacy of ketamine is rapid and takes effect within hours or minutes, unlike the standard of care selective serotonin reuptake inhibitors (SSRIs) which require several weeks to have an effect. Further, there are patients who respond to the antidepressant effects of ketamine but do not respond to SSRIs.

The compounds (2R,6R)-hydroxynorketamine (HNK) and (2S,6S)-hydroxynorketamine are analogs of ketamine which may be useful for treatment of pain, depression, anxiety, and related disorders. Thus, the need for practical and efficient methods of synthesis of these compounds, and for stable polymorphs with good pharmaceutical properties exists. The present disclosure fulfills this need and provides additional advantages set forth herein.

FIELD OF THE DISCLOSURE

This disclosure provides free base forms of (2R,6R)-hydroxynorketamine (HNK) and (2S,6S)-hydroxynorketamine, and crystal forms of the corresponding hydrochloride salts. The disclosure also provides practical and efficient methods for producing (2R,6R)-HNK, (2S,6S)-HNK, (2S, 6R)-HNK and (2R, 6S)-HNK. The disclosure further provides methods of producing 2R,6R-HNK and 2S,6S-HNK crystal forms, crystal forms of the corresponding hydrochloride salts, and a method of recrystallizing 2R,6R-HNK hydrochloride salt.

SUMMARY

The disclosure includes a method for the manufacture of (2R,6R)-hydroxynorketamine or salt thereof and a method for the manufacture of (2S,6S)-hydroxynorketamine, or a salt thereof, the method comprising

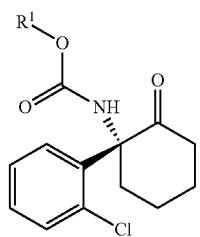

Formula Ia

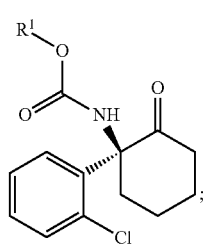

Formula Ib (i) treating a compound of Formula Ia or Formula Ib with a base, then with a trialkylsilylchloride, then with a peroxy compound, and then optionally with an acid or a fluoride source, to provide a compound of Formula IIa if Formula Ia was treated or a compound of Formula IIb if Formula Ib was treated, wherein the compound of Formula IIa or Formula IIb contains a carbamate linkage;

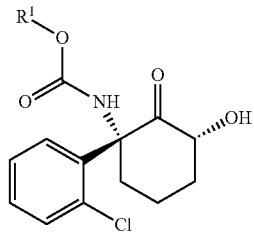

Formula IIa

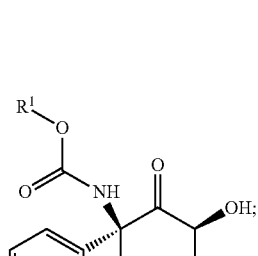

Formula IIb and (ii) cleaving the carbamate linkage in the compound of Formula IIa or Formula IIb to provide (2R,6R)-hydroxynorketamine if the carbamate linkage of the compound of Formula IIa was cleaved, or (2S,6S)-hydroxynorketamine if the carbamate linkage of the compound of Formula IIb was cleaved

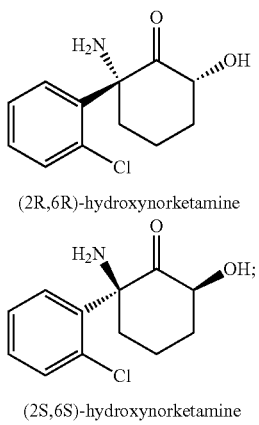

(2R,6R)-hydroxynorketamine (2S,6S)-hydroxynorketamine wherein $R^1$ is $C_1$-$C_6$ alkyl, $C_1$-$C_6$haloalkyl, benzyl, 4-methoxybenzyl, or 2-trimethylsilylethyl. When $R^1$ is t-butyl particularly good yields are achieved. The use of chiral starting material provides the advantage of obtaining an enantiomerically pure product.

The disclosure includes crystalline forms of (2R,6R)-hydroxynorketamine hydrochloride and (2S,6S)-hydroxynorketamine hydrochloride.

The disclosure includes a crystalline form of (2R,6R)-hydroxynorketamine hydrochloride characterized by single crystal parameters approximately equal to the following:

cell dimensions comprising a=7.3549(6) Å alpha=90°
b=7.4932(5) Å beta=96.868(2°)
c=11.3498(8) Å gamma=90°
V=621.02(8) Å$^3$; and space group=P 1 21 1, crystal system=monoclinic, molecules per unit cell=1, density (calculated)=1.477 Mg/m$^3$. The number in parentheses indicates the uncertainty in the last digit for the crystal used for this crystal structure determination. However, when multiple crystallizations of 2R,6R-HNK were performed, the variability in cell dimensions was slightly larger though the 2R,6R-HNK was still crystallized in the same space group and system. When a crystalline form of 2R,6R-HNK is claimed by unit cell dimensions the claim encompasses all crystalline forms of 2R,6R-HNK in the same space group and system, having unit cell dimensions a, b, and c as stated +/−0.1 Å and a cell volume as stated +/−2 Å$^3$.

The disclosure also includes a crystalline form of (2S,6S)-hydroxynorketamine hydrochloride characterized by single crystal parameters approximately equal to the following:

cell dimensions comprising a=7.3493(8) Å alpha=90°
b=7.4846(8) Å beta=96.866(3°)
c=11.3404(12) Å gamma=90°
V=619.32(12) Å$^3$; and space group=P 1 21 1, crystal system=monoclinic, molecules per unit cell=1, density (calculated)=1.481 Mg/m$^3$. When a crystalline form of 2S,6S-HNK is claimed by unit cell dimensions the claim encompasses all crystalline forms of 2S,6S-HNK in the same space group and system, having unit cell dimensions a, b, and c as stated +/−0.1 Å and a cell volume as stated +/−2 Å$^3$.

The disclosure also includes a crystalline form of (2R,6R)-hydroxynorketamine hydrochloride that contains no detectable amounts of other hydroxynorketamine or hydroxynorketamine salts crystalline forms as determined by x-ray powder diffraction and a crystalline form of (2S,6S)-hydroxynorketamine hydrochloride that contains no detectable amounts of other hydroxynorketamine or hydroxynorketamine salts crystalline forms as determined by x-ray powder diffraction.

DETAILED DESCRIPTION

Figure 1:
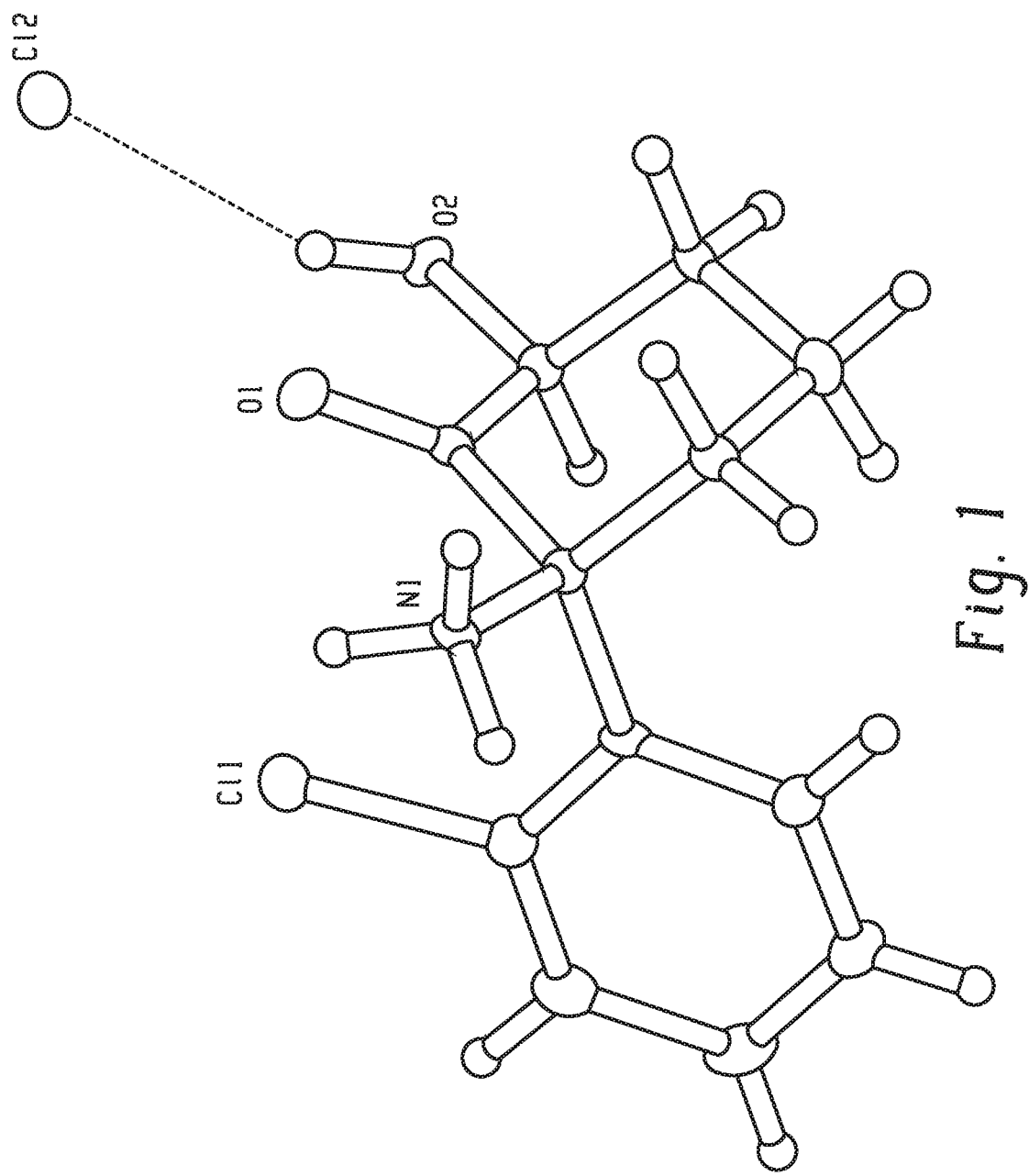
FIG. 1 is a single crystal x-ray structure of (2S,6S)-hydroxynorketamine hydrochloride.

This disclosure provides the first reported synthetic methods for the production of enantiomerically pure 2R,6R-HNK and enantiomerically pure 2S,6S-HNK. The (2R,6R)-2-amino-2-(2-chlorophenyl)-6-hydroxycyclohexanone ((2R,6R)-hydroxynorketamine (HNK)) ketamine metabolite has the structure

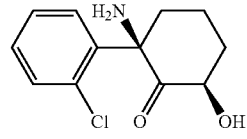 [SMILES: N[C@@]1(c2ccccc2Cl)CCC[C@@H](O)C1=O]

The (2S,6S)-2-amino-2-(2-chlorophenyl)-6-hydroxycyclohexanone ((2S,6S)-hydroxynorketamine (HNK)) ketamine metabolite has the structure

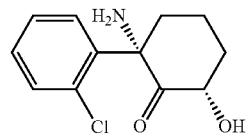

This disclosure provides pure crystal forms of (2R,6R)-hydroxynorketamine ((2R,6R)-HNK) and (2S,6S)-hydroxynorketamine ((2S,6S)-HNK) hydrochloride salts. The compounds (2R,6R)-hydroxynorketamine and (2S,6S)-hydroxynorketamine can be synthesized using the similar reaction sequences, but starting from opposite enantiomers of norketamine. Details of the methods for producing pure HCl crystalline forms and results supporting these showings can be found in the Examples section.

Terminology

Compounds disclosed herein are described using standard nomenclature. Unless defined otherwise, all technical and scientific terms used herein have the same meaning as is commonly understood by one of skill in the art to which this disclosure belongs.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and the terms "heteroatom-containing alkyl" and "heteroalkyl" refer to an alkyl substituent in which at least one carbon atom is replaced with a heteroatom, as described in further detail infra. "haloalkyl" refers to alkyl substituted with one or more halogens. If not otherwise indicated, the terms "alkyl" and "lower alkyl" include linear, branched, cyclic, unsubstituted, substituted, and/or heteroatom-containing alkyl or lower alkyl, respectively.

"Alkoxy" indicates an alkyl group as defined above with the indicated number of carbon atoms attached through an oxygen bridge (—O—). Examples of alkoxy groups include methoxy, ethoxy, n-propoxy, isopropoxy, and the like. "Haloalkoxy" refers to alkoxy groups substituted with one or more halogens.

The term "chiral" refers to molecules, which have the property of non-superimposability of the mirror image partner.

The term "carbamate linkage" refers to the linking group "—O—(CO)—NR—", and "cleaving" the carbamate linkage produces a compound with "RNH—" in place of the carbamate linkage.

"Stereoisomers" are compounds, which have identical chemical constitution, but differ with regard to the arrangement of the atoms or groups in space.

A "Diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

The terms "halo" and "halogen" are used in the conventional sense to refer to a chloro, bromo, fluoro or iodo substituent.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

Where a compound exists in various tautomeric forms, the invention is not limited to any one of the specific tautomers, but rather includes all tautomeric forms.

The disclosure includes compounds having all possible isotopes of atoms occurring in the compounds. Isotopes include those atoms having the same atomic number but different mass numbers. By way of general example, and without limitation, isotopes of hydrogen include tritium and deuterium and isotopes of carbon include 11C, $^{13}$C, and $^{14}$C.

A "patient" means any human or non-human animal in need of medical treatment. Medical treatment can include treatment of an existing condition, such as a disease or disorder, prophylactic or preventative treatment in patients known to be at risk for experiencing symptoms of anxiety or depression, or diagnostic treatment. In some embodiments the patient is a human patient.

As used herein "halide" is chloride, bromide, or iodide.

HPLC as used herein is high performance liquid chromatography utilizing refractive index detection with the method described in the Experimental Section.

Percent pure (% purity" refers to) the area percentage obtained from dividing the area of the desired HPLC peak by the sums of areas for the desired HPLC peak and the HPLC peaks of each reaction impurity and multiplying this dividend by 100.

"Percent Yield or isolated yield (% yield)' is the weight of the isolated product(s) divided by the molecular weight of the isolated products divided by the moles of starting material used in the reaction.

"Reaction Impurities" are process related impurities (by products) including all residual starting materials, residual intermediates, and other reaction products other than desired product detected by HPLC. The FDA uses the term "process related impurities" to describe impurities derived from the manufacturing process.

"Stereoselective" is any reaction that results in less than 10% of the undesired epimeric byproduct.

The term "enantioenriched" is used to indicate that, where a compound may exist as two or more enantiomers, one of the enantiomers is present in excess of the other(s). For example, where two enantiomers of a compound are possible, an enantioenriched sample may include greater than 50%, greater than 60%, greater than 70%, greater than 75%, greater than 80%, greater than 85%, greater than 90%, greater than 95%, or greater than 99% of one of the enantiomers. A process is "enantioenriching" or "enantioselective" when the process favors production of one enantiomer over production of another enantiomer. Similarly, the term "diastereomerically enriched" is used to indicate that, where a compound may exist as two or more diastereomers, one of the diastereomers is present in excess of the other(s). For example, where two diastereomers of a compound are possible, a diastereomerically enriched sample may include greater than 50%, greater than 60%, greater than 70%, greater than 75%, greater than 80%, greater than 85%, greater than 90%, greater than 95%, or greater than 99% of one of the diastereomers. A process is "diastereomerically enriching" or "diastereoselective" when the process favors production of one diastereomer over production of another diaseteomer.

Unless otherwise specified, reference to an atom is meant to include isotopes of that atom. For example, reference to H is meant to include $^1H$, $^2H$ (i.e., D) and $^3H$ (i.e., T), and reference to C is meant to include $^{12}C$ and all isotopes of carbon (such as $^{13}C$).

The transitional phrases "comprising," "consisting essentially of," and "consisting of," carry the means accorded these terms by current patent law. All embodiments claimed with one of the transitional phases may also be claimed using the other transitional phrases. For example, an embodiment claimed with "comprising" as the transitional phrase also include embodiments that may be claimed with "consisting essentially of" or "consisting of" transitional language and vice versa.

Chemical Description

The structure of (2R, 6R)-hydroxynorketamine, IUPAC name (2R,6R)-2-amino-2-(2-chlorophenyl)-6-hydroxycyclohexanone, is:

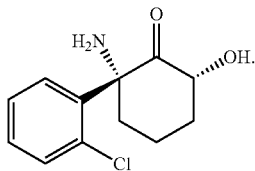 [SMILES: N[C@@]1(c2ccccc2Cl)CCC[C@@H](O)C1=O]

The structure of (2S, 6S)-hydroxynorketamine, IUPAC name (2S,6S)-2-amino-2-(2-chlorophenyl)-6-is hydroxycyclohexanone, is:

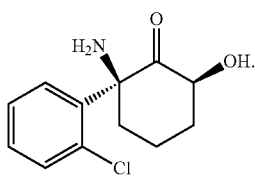 [SMILES: N[C@]1(c2ccccc2Cl)CCC[C@H](O)C1=O]

The methods herein are stereospecific. This means that if the synthesis starts with (R)-norketamine, the synthesis will pass through the intermediates Formula Ia and Formula IIa and end with the final product (2R,6R)-hydroxynorketamine ((2R,6R)-HNK). Similarly, if the synthesis starts with (S)-norketamine, the synthesis will pass through the intermediates Formula Ib and Formula IIb and end with the final product (2S,6S)-hydroxynorketamine ((2S,6S)-HNK). The stereospecific nature of the synthetic methods is illustrated below.

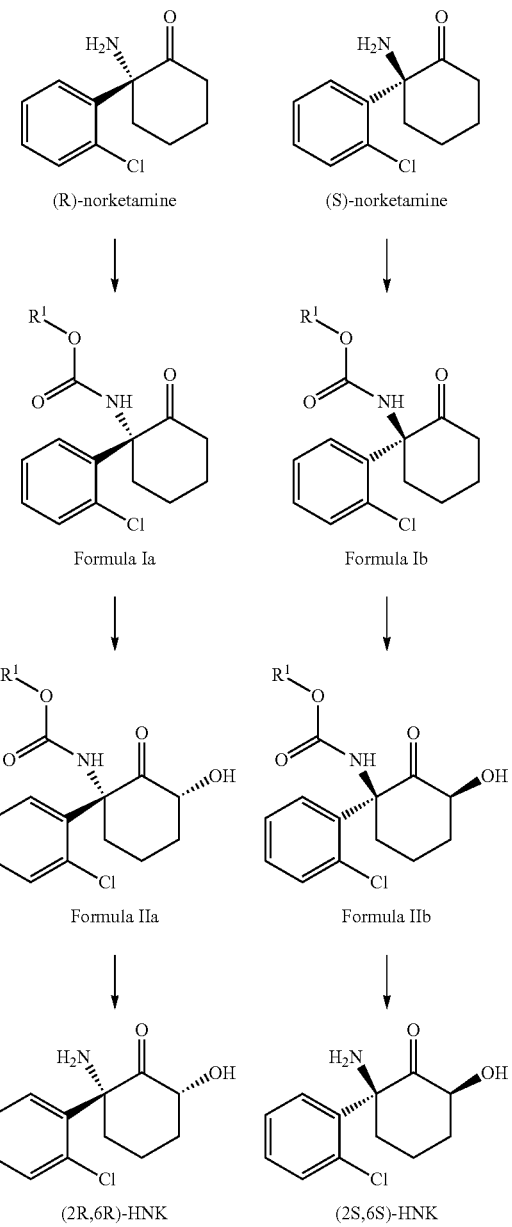

The disclosure provides a method for the manufacture of (2R,6R)-hydroxynorketamine or (2S,6S)-hydroxynorketamine, or a salt thereof, the method including generating a compound of Formula Ia or Formula Ib from norketamine Formula Ia

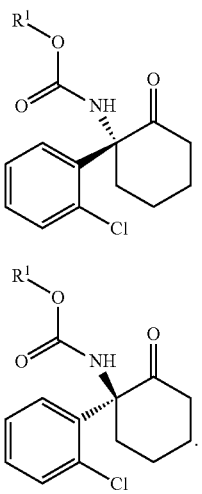

Formula Ib wherein IV is $C_1$-$C_6$ alkyl, $C_1$-$C_6$ haloalkyl, benzyl, 4-methoxybenzyl, or trimethylsilylethyl. In certain embodiments IV is a tert-butyl group. (R)-norketamine can be accessed via chiral resolution from racemic norketamine via a chiral resolution with L-pyroglutamic acid (or the tartaric acid).

(R)-norketamine can be reacted with a carbamate-forming reagent to produce the carbamate compound Formula Ia, and (S)-norketamine can be reacted with a carbamate-forming reagent to produce the carbamate compound Formula Ib. The goal is to produce a carbamate which can protect the amine during some subsequent steps, and then be deprotected when protection is no longer needed. The carbamate reagent can be a dialkyldicarbonate such as di-tert-butyldicarbonate, or an alkylhaloformate such as methyl chloroformate, ethyl chloroformate, or tert-butyl chloroformate. The carbamate reagent can be other chloroformates such as bromoethylchloroformate, benzylchoroformate, 4-methoxybenzylchloroformate, or trimethylsilylethylchloroformate. This reaction could be performed with a variety of bases, including carbonate bases such as potassium carbonate, lithium carbonate, sodium carbonate, or sodium bicarbonate, hydroxide bases such as lithium hydroxide, sodium hydroxide, or potassium hydroxide, amine bases such as trimethylamine, trimethylamine, diisopropylethylamine, 1,5-diazabicyclo[4.3.0]non-5-ene (DBN), or 1,8-diazabicyclo[5.4.0]undec-7-ene (DBU), or a combination of the foregoing, or with no base at all. A wide variety of solvents can be used, including toluene, ethyl acetate, methylene chloride, water, or combinations of the above.

In an embodiment, generating the compound of Formula Ia or Formula Ib includes reacting (R)-norketamine with $(R^1O_2C)_2O$ or $R^1O_2C$—X to generate a compound of Formula Ia, or reacting (S)-norketamine with $(R^1O_2C)_2O$ or $R^1O_2C$—X to generate a compound of Formula Ib; wherein X is a halogen.

In an embodiment, $R^1$ is tert-butyl, and generating the compound of Formula Ia includes reacting (R)-norketamine with (tert-butyl-$O_2C)_2O$, and generating the compound of Formula Ib includes reacting (S)-norketamine with (tert-butyl-$O_2C)_2O$.

The disclosure provides a method for the manufacture of (2R,6R)-hydroxynorketamine or (2S,6S)-hydroxynorketamine, or a salt thereof, the method including treating the compound of Formula Ia or Formula Ib with a strong base, then with a trialkylsilylchloride, then with a peroxy compound, and then optionally with an acid or a fluoride source, to provide a compound of Formula IIa if Formula Ia was treated or a compound of Formula IIb if Formula Ib was treated Formula IIa

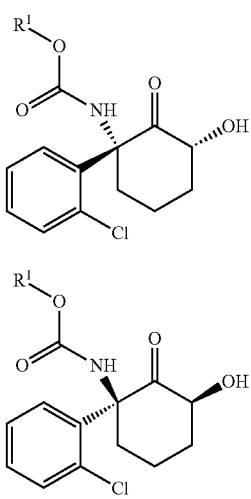

Formula IIb wherein $R^1$ is $C_1$-$C_6$ alkyl, $C_1$-$C_6$ haloalkyl, benzyl, 4-methoxybenzyl, or trimethylsilylethyl.

A compound of Formula IIa or Formula IIb is treated with a base to produce an intermediate which is believed to be a silyl enol ether, but is used in the next reaction without characterization. While not wanting to be bound by theory, it is believed that the base removes a proton alpha to the carbonyl of the compound of Formula IIa or Formula IIb, generating an enolate, and the enolate then reacts on its oxygen atom with trialkylsilyl chloride to generate the silyl enol ether.

The disclosure provides methods of producing 2R,6R-HNK and 2S,6S-HNK crystal forms and crystal forms of the corresponding hydrochloride salts.

The disclosure also provides a method of obtaining 2R,6R-hydroxynorketamine HCl by recrystallization from crude or semicrude 2R,6R-hydroxynorketamine HCl by means of dissolving the crude 2R,6R-hydroxynorketamine HCl in water, then adding acetone at a constant flow rate, which allows for the precipitation of the purified 2R,6R-hydroxnorketamine HCl. 2R,6R-hydroxynorketamine has been previously described in the literature and has been noted for its antidepressant activity. To date, no recrystallization method has been described in the literature for the compound or any of its salt formulations.

The disclosure provides 2R,6R-hydroxynorketamine hydrochloride recrystallized from crude, semicrude, or purified 2R,6R-hydroxynorketamine hydrochloride. Two notable issues may occur in the late stage formation of 2R,6R-HNK. The first is the presence of minor byproduct impurities which cannot be removed easily by standard methods. The second is the "trapping" of organic solvent in the final salt formation. These "trapped" solvents cannot be removed by standard methods (vacuum, heating under vacuum, etc.) which results in a small percentage of organic solvent within the final product. This recrystallization method reduces the impurity levels, and critically removes the solvent level within the final 2R,6R-hydroxynorketamine hydrochloride product. Thus the disclosure provides a method of purifying 2R,6R-HNK, in which 2R,6R-Hydroxynorketamine hydrochloride is dissolved in an equal mass of water (1 g/1 g). Under magnetic stirring, 20 volume equivalents (20 nil per 1 gram) of acetone are added at a constant flow rate of 0.75 equivalents per minute, while stirring the solution. The resulting suspension is stirred a further 1.5 hours, then filtered, and vacuum dried over 16 hours at room temperature to give the final product.

Thus an embodiment of the disclosure includes dissolving solid and preferably crystalline 2R,6R-HNK hydrochloride in approximately and equal mass of water (1 g compound/1-1.2 grams water), adding approximately 20 volumes of solvent, or 15 to 25 volumes of solvent, preferably acetone at a constant flow rate, with stirring to form a suspension, followed by filtration to form a filtrate, and vacuum drying. In certain embodiments the suspension is stirred for 1-4 hours, or 1-2 hours after the addition of solvent is complete. In certain embodiments the filtrate is dried more than 8 hours, more than 12 hours, 12-20 hours or about 16 hours.

The disclosure further provides additional synthetic methods that are variations of the methods described above for producing 2,6-HNK or intermediates useful for producing the various enantiomers of 2,6-HNK.

In one such method, 2-Chlorophenyl cyclopentylketone can be used to generate (R)- or (S)-norketamine. The disclosure provides a cost efficient method for producing 2-chlorophenyl cyclopentylketone starting material by first forming tosyl hydrazide, followed by reaction with 2-chlorobenzaldehyde. This reaction is shown in Scheme 1.

This disclosure also provides a method of using diphenyl ether (Scheme 2), as opposed to the published route, which uses DowTherm A, to allow the thermal rearrangement at slightly lower temperatures.

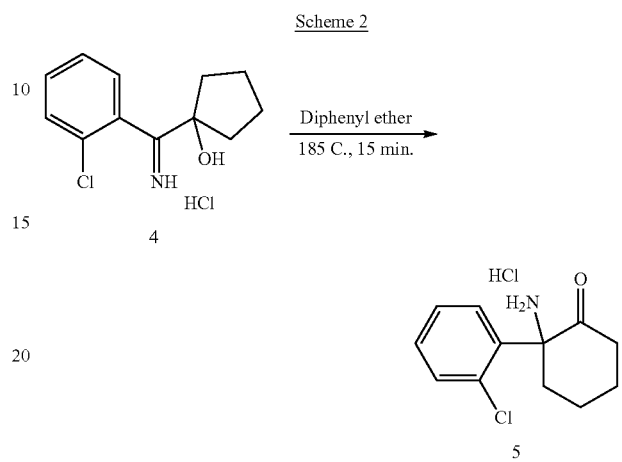

This disclosure provides a modified deprotection of the Rubottom oxidation product that uses formic (Scheme 3). Earlier methods employed tetrabutylammonium fluoride to effect the deprotection.

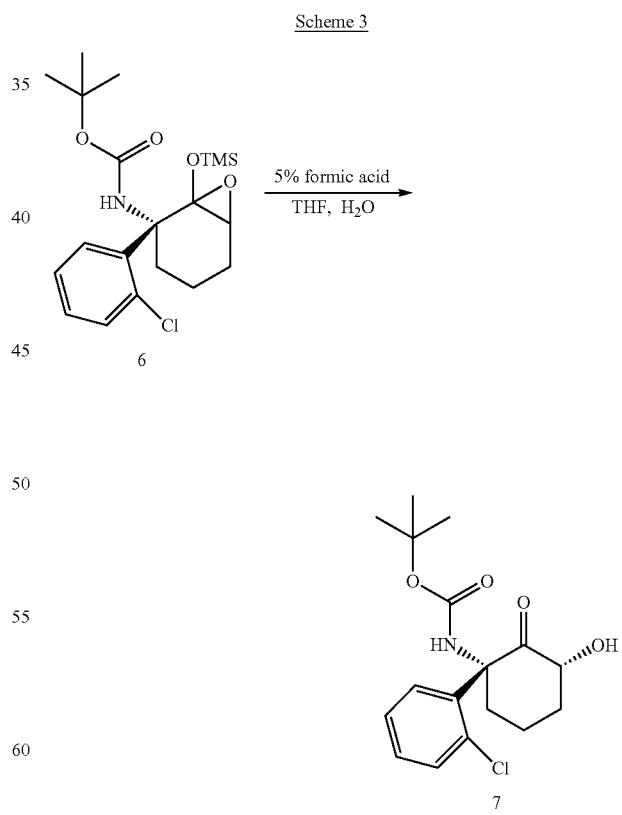

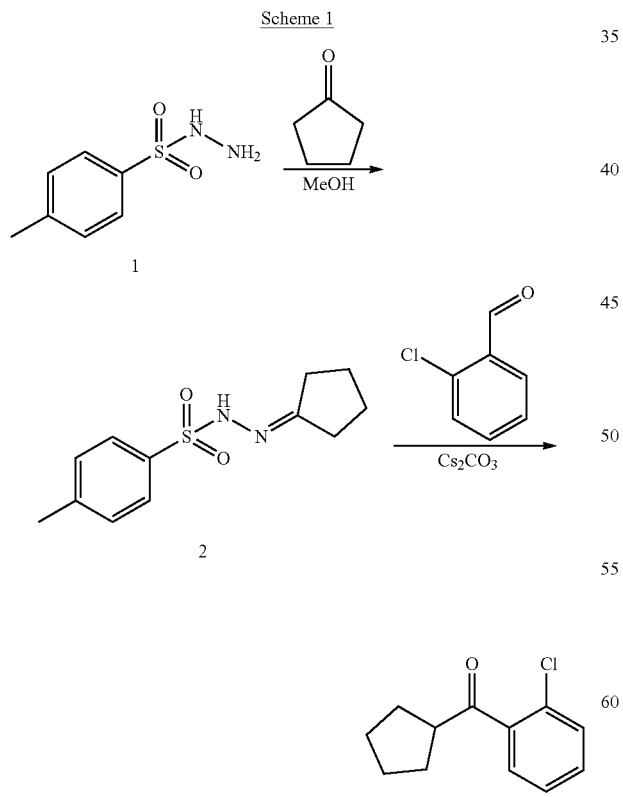

The disclosure also provides a method of using hydrochloric acid in ethyl acetate for the final deprotection (Scheme 4). This directly forms the desired HCl salt.

Scheme 4

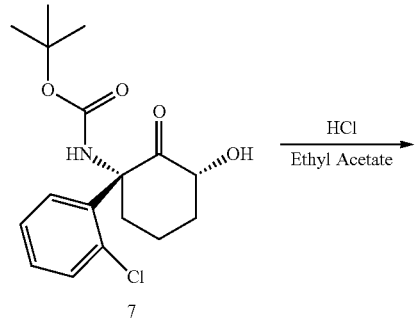

The disclosure also provides a synthesis of 2R,6S-hydroxynorketamine and 2S,6R-hydroxynorketamine. While the 2R,6S-hydroxynorketamine compound is known in the literature, the disclosure provides a synthetic route that is a vast improvement in time, yield, and reproducibility. 2R,6S-hydroxynorketamine has been noted to have antidepressant effects in the forced swim test equal to or greater than that of 2R,6R hydroxynorketamine, however the stability of 2R,6S-hydroxynorketmine is problematic. The route (Scheme 5) involves the triflation of enantiopure compound 8, followed by inversion of the alcohol with the anion of nitrobenzoic acid. Then cleavage of the nitrobenzoate group and careful deprotection of the BOC group yields the desired 2R,6S-hydroxynorketamine. This route has also been applied to its enantiomer.

Scheme 5

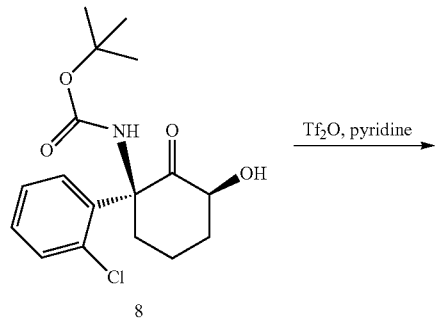

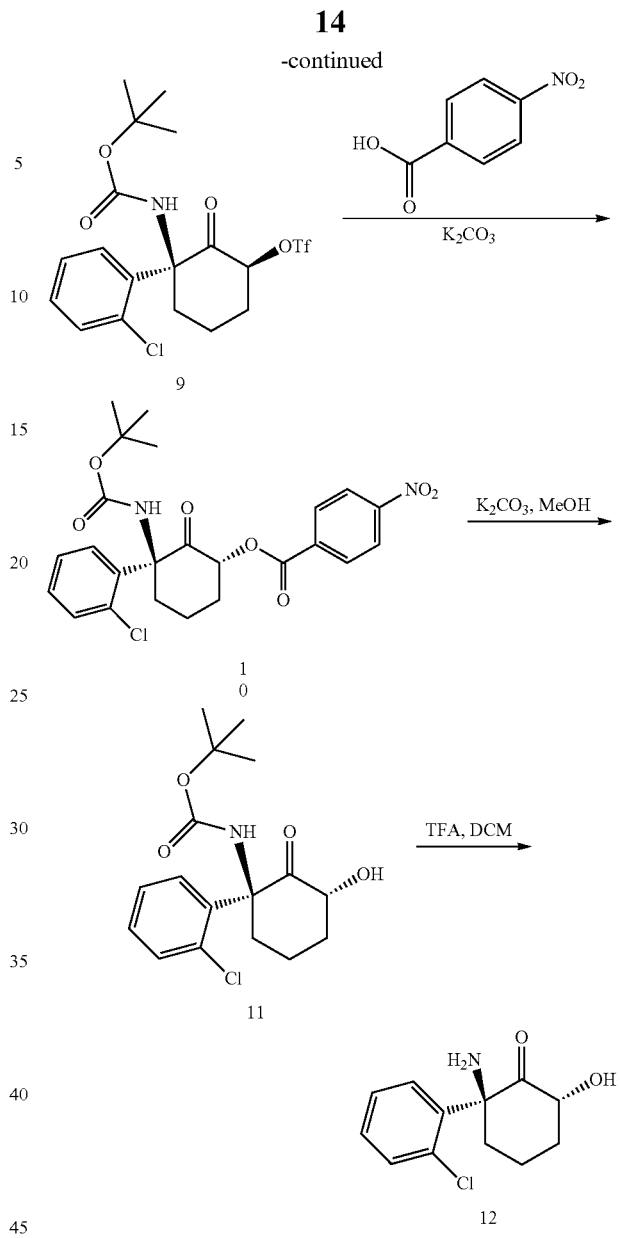

Thus, the disclosure provides a method of preparing 2R,6S-hydroxynorketamine comprising triflation of tert-butyl ((1S,3S)-1-(2-chlorophenyl)-3-hydroxy-2-oxocyclohexyl)carbamate (8), followed by inversion of the alcohol with the anion of nitrobenzoic acid, cleavage of the nitrobenzoate group, and removal of the BOC protecting group to produce 2R,6S-HNK.

The disclosure provides a method of preparing 2R,6S-HNK comprising (i) triflation of entiopure isopropyl ((1S,3S)-1-(2-chlorophenyl)-3-hydroxy-2-oxocyclohexyl)carbamate 8 to form (1S,3S)-3-((tert-butoxycarbonyl)amino)-3-(2-chlorophenyl)-2-oxocyclohexyl trifluoromethanesulfonate. In some embodiments the triflation is conducted in the presence of pyridine in a non-polar solvent such as dichloromethane or other solvent. The reaction may be quenched, for example by adding sodium bicarbonate. The solvent may be removed by evaporation or other means to form crude triflate 9.

The method of preparing 2R,6S-hydroxynorketamine further comprises (ii) dissolving the crude triflate in DMF or other aprotic solvent such as NMP, followed by addition of 4-nitrobenzoic acid and weak base, such as potassium carbonate or sodium carbonate. In certain embodiments the product is extracted with aqueous solution and the organic phase evaporated to provide (1S,3R)-3-((tert-butoxycarbonyl)amino)-3-(2-chlorophenyl)-2-oxocyclohexyl 4-nitrobenzoate 10.

This method further comprises (iii) cleavage of the nitrobenzoate group by dissolving the nitrobenzoate 10 in methanol, or other suitable solvent such as ethanol, followed by addition of potassium carbonate or other carbonate salt to produce protected 2R,6S-HNK, 11. In some embodiments the protected 2R,6S-HNK is washed with aqueous solution and aqueous saturated salt solution such as saturated sodium chloride.

The method of preparing 2R,6S-HNK further comprises (iv) gently deprotecting the protected 2R,6S-HNK, 11, in nonpolar solvent such as DCM and adding acid, such at trifluoroacetic acid. The solvent and acid may be removed by evaporation, such as rotary evaporation. In some embodiments the product, 2R,6S-HNK, 12, is washed by extraction in ethyl acetate and aqueous neutral solution, such as a pH7 potassium phosphate buffered solution, to the crude material. The purified material may be obtained from the organic phase by evaporation.

Steps (i) to (iv) may also be employed to produce 2S,6R-HNK by starting with the ((1R,3R)-1-(2-chlorophenyl)-3-hydroxy-2-oxocyclohexyl)carbamate 8 Å enantiomer.

A variety of bases can be used to remove the proton alpha to the carbonyl in Formula I during the reaction which provides a compound of Formula II. These bases include strong bases such as lithium diisopropylamide, sodium hexamethyldisilazane, potassium hexamethyldisilazane, or various alkyllithium reagents such as sec-butyllithium. Under some conditions weaker bases could be used, including carbonate bases such as potassium carbonate, lithium carbonate, sodium carbonate, or sodium bicarbonate, hydroxide bases such as lithium hydroxide, sodium hydroxide, or potassium hydroxide, amine bases such as trimethylamine, trimethylamine, diisopropylethylamine, 1,5-diazabicyclo[4.3.0]non-5-ene (DBN), or 1,8-diazabicyclo[5.4.0]undec-7-ene (DBU). When strong bases are used the proton removal should be performed at a temperature below 25° C., preferably below 0° C., more preferably below −50° C., and can be in a range of −50° C. to −85° C. When weaker bases are used the temperature could be in a wide range, from −25° C. to 100° C. The compound of Formula IIa or Formula IIb should be stirred with the base for a time period sufficient to remove the proton alpha to the carbonyl, and this time period can be from 5 minutes to 24 hours depending on the conditions and base used. The solvent for this step should be one that does not appreciably react with the base under the conditions used. When strong bases are used, suitable solvents include tetrahydrofuran, diethylether, methyl-tert-butylether, and the like. When weaker bases are used, a wide variety of solvents can be used including tetrahydrofuran, diethylether, methyl-tert-butylether, methylene chloride, toluene, N,N-dimethylformamide, and the like.

In an embodiment, treating the compound of Formula Ia or Formula Ib with a strong base includes treating the compound of Formula Ia or Formula Ib with lithium diisopropylamide at a temperature below −50° C.

Following the removal (or possibly during the removal) of the proton alpha to the carbonyl of the compound of Formula Ia or Formula Ib, trialkylsilylchloride is added to react with the intermediate enolate and is believed to form a silyl enol ether. This reaction may be performed for a period of time from 5 minutes to 24 hours, and at a temperature from −78° C. to 100° C., depending on the conditions. In some embodiments, the trialkylsilyl chloride is added at the same time as the base, such that the removal of the proton alpha to the carbonyl and the reaction of the resulting enolate with trialkylsilyl chloride are occurring as a continuous process. The trialkylsilyl chloride can be trimethylsilyl chloride, triethylsilyl chloride, tert-butyldimethylsilyl chloride, triisopropylsilyl chloride, and the like.

In an embodiment, the trialkylsilylchloride is trimethylsilyl chloride.

Once the silyl enol ether is formed, it is treated with a peroxy compound and then optionally with an acid or a fluoride source to provide a compound of Formula IIa or Formula IIb. The peroxy compound can be a peroxy acid such as peroxybenzoic acid or peracetic acid, or a peroxide such as dimethyldioxirane, tert-butylhydroperoxide, or hydrogen peroxide. The treatment with the peroxy compound can be performed in a variety of solvents and at a variety of temperatures and reaction times. For example, the treatment with peroxy compound can be performed in dichloromethane or chloroform for 5 minutes to 24 hours, and can be at a temperature from −30° C. to 50° C.

In an embodiment, the peroxy compound is meta-chloroperoxybenzoic acid.

In some embodiments following the treatment with peroxy compound, an acid or fluoride source is added to produce a compound of Formula IIa or Formula IIb. While not wanting to be bound by theory, the peroxy compound treatment is believed to generate an alpha-siloxyepoxide, and the acid or fluoride source cleaves the silicon oxygen bond in the alpha siloxyepoxide to produce an alpha-hydroxyepoxide, which then ring opens to provide alpha-hydroxyketone product Formula IIa or Formula IIb. The fluoride source can be any fluoride-containing reagent that is capable of breaking the silicon-oxygen bond, and could include sodium fluoride, potassium fluoride, cesium fluoride, tetra-n-butylammonium fluoride, hydrogen fluoride-pyridine, and the like. The addition of a fluoride source can be performed in a variety of solvents and at a variety of temperatures and reaction times. For example, the treatment with a fluoride source can be performed in tetrahydrofuran, diethylether, or methyl-tert-butylether, for 5 minutes to 24 hours, and can be at a temperature from −30° C. to 50° C. In some embodiments, the silicon-oxygen bond can be broken without a fluoride source, such as by treatment by acid, which could include treatment with hydrochloric, sulfuric, acetic, or trifluoroacetic acids, and the like. In some embodiments, there is no treatment of the alpha siloxyepoxide with either acid or fluoride source, but the desired product is still produced.

In some embodiments, after treatment with peroxy compound the compound of Formula Ia or Formula Ib is treated with tetra-n-butylammonium fluoride.

The disclosure provides a method for the manufacture of (2R,6R)-hydroxynorketamine or (2S,6S)-hydroxynorketamine, or a salt thereof, the method including cleaving the carbamate linkage in Formula IIa or Formula IIb to provide (2R,6R)-hydroxynorketamine if the carbamate linkage of Formula IIa was cleaved, or (2S,6S)-hydroxynorketamine if the carbamate linkage of Formula IIb was cleaved

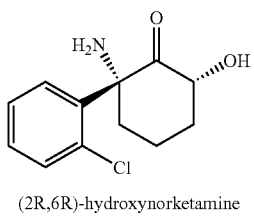

(2R,6R)-hydroxynorketamine

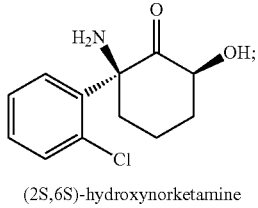

(2S,6S)-hydroxynorketamine wherein IV is $C_1$-$C_6$ alkyl, $C_1$-$C_6$ haloalkyl, benzyl, 4-methoxybenzyl, or trimethylsilylethyl.

The method of cleaving the carbamate linkage depends on the nature of $R^1$. Any carbamate with one of the listed $R^1$ groups can be cleaved by mild base. If $R^1$ is tert-butyl, then acid can be used to cleave the tert-butyl carbamate linkage. Acids which can be used for this step include hydrochloric, sulfuric, and acetic acids, such as trifluoroacetic acid. If IV is a 2-haloalkyl, such as 2-bromoethyl or 2,2,2-trichloroethyl, the carbamate linkage can be cleaved by treatment with zinc. If IV is benzyl, the carbamate linkage can be cleaved by hydrogenation, if $R^1$ is 4-methoxybenzyl then the carbamate linkage can be cleaved by hydrogenation or oxidation, and if $R^1$ is 2-trimethylsilylethyl, then the carbamate linkage can be cleaved by treatment with fluoride. If any of these treatments produce an acid salt of the product, the resulting salt can then be converted to the free base using a base, such as potassium carbonate, lithium carbonate, sodium carbonate, or sodium bicarbonate, lithium hydroxide, sodium hydroxide, potassium hydroxide, trimethylamine, trimethylamine, diisopropylethylamine, 1,5-diazabicyclo[4.3.0]non-5-ene (DBN), or 1,8-diazabicyclo[5.4.0]undec-7-ene (DBU). Preferably a carbonate base such as sodium bicarbonate is used. The resulting free base can then be treated with hydrochloric acid to produce the (2R,6R)-hydroxynorketamine hydrochloride salt or (2S,6S)-hydroxynorketamine hydrochloride salt. Other acids can be used to make other salts of (2R,6R)-hydroxynorketamine or (2S,6S)-hydroxynorketamine.

In an embodiment, $R^1$ is tert-butyl and cleaving the carbamate linkage includes treatment with acid.

In an embodiment, $R^1$ is tert-butyl and cleaving the carbamate linkage includes treatment with trifluoroacetic acid.

In an embodiment, a hydrochloride salt is manufactured, and the method additionally includes treating (2R,6R)-hydroxynorketamine with hydrochloric acid to manufacture (2R,6R)-hydroxynorketamine hydrochloride salt, or treating (2S,6S)-hydroxynorketamine with hydrochloric acid to manufacture (2S,6S)-hydroxynorketamine hydrochloride salt.

In an embodiment, a method for the manufacture of (2R,6R)-hydroxynorketamine, or a salt thereof, includes generating a compound of Formula Ia

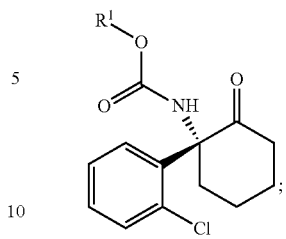

Formula Ia treating the compound of Formula Ia with lithium diisopropylamide at below −50° C., then with trimethylsilyl chloride, then with meta-chloroperoxybenzoic acid, and then with tetra-n-butylammonium fluoride, to provide a compound of Formula IIa

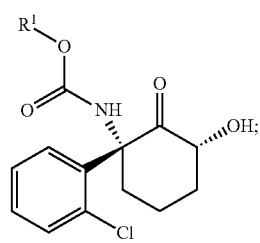

Formula IIa and
cleaving the carbamate linkage in Formula IIa by treatment with acid to provide (2R,6R)-hydroxynorketamine

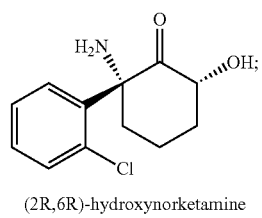 [SMILES: N[C@@]1(c2ccccc2Cl)CCC[C@@H](O)C1=O]

(2R,6R)-hydroxynorketamine wherein $R^1$ is tert-butyl.

In an embodiment, a hydrochloride salt is manufactured.

In an embodiment, a method for the manufacture of (2S,6S)-hydroxynorketamine, or a salt thereof, includes generating a compound of Formula Ib

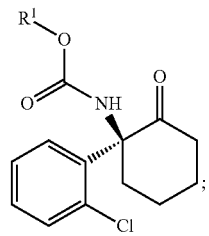

Formula Ib treating the compound of Formula Ib with lithium diisopropylamide at below −50° C., then with trimethylsilyl chloride, then with meta-chloroperoxybenzoic acid, and then with tetra-n-butylammonium fluoride, to provide a compound of Formula IIb

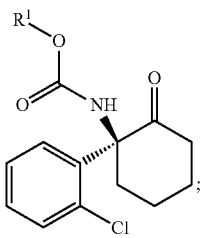

Formula IIb and cleaving the carbamate linkage in Formula IIb, wherein $R^1$ is tert-butyl, by treatment with acid to provide (2S,6S)-hydroxynorketamine

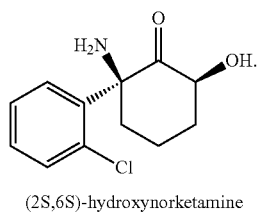 [SMILES: N[C@]1(c2ccccc2Cl)CCC[C@H](O)C1=O]

(2S,6S)-hydroxynorketamine (2S,6S)-hydroxynorketamine and (2R,6R)-hydroxynorketamine are prepared according to the following synthesis in Scheme 6, which shows the synthesis of (2S,6S)-hydroxynorketamine. The details of (2S,6S)-HNK and (2R,6R)-HNK synthesis are given in Examples 1-8. The compound numbers shown in the (2S,6S)-HNK synthetic route are used in the examples.

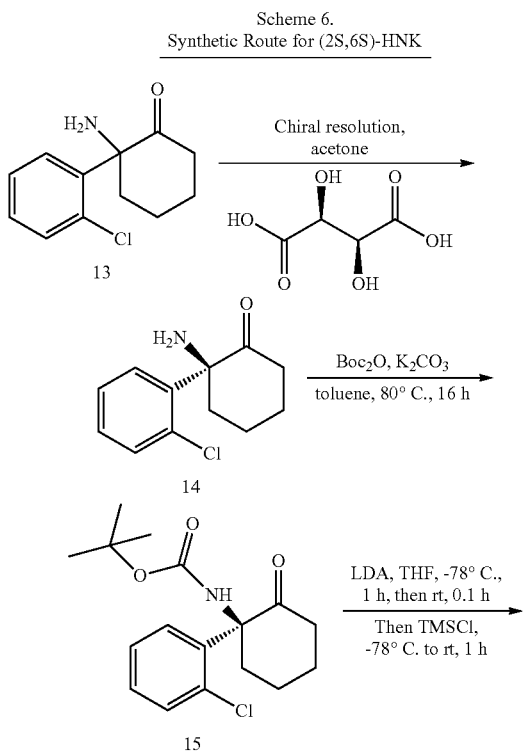

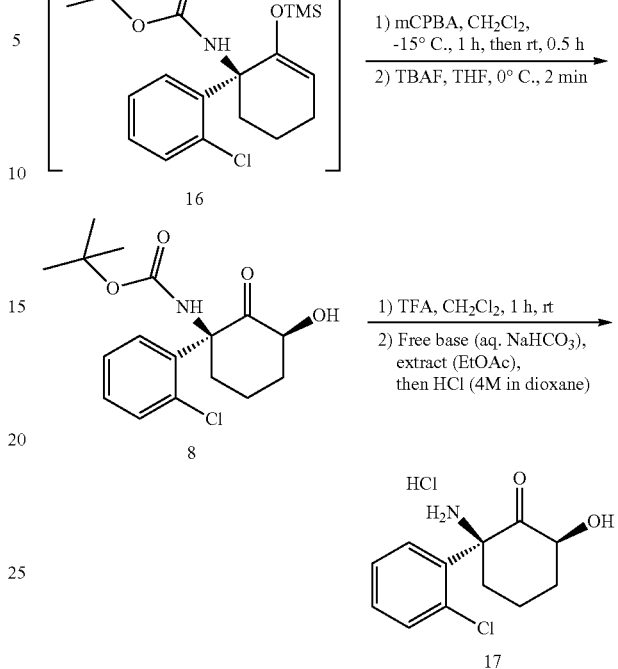

Scheme 7 shows the synthetic route for 6,6-dideuteroketamine hydrochloride. The details of the deuteration are provided in Example 9.

Scheme 7.
Synthetic route for 6,6-dideuteroketamine hydrochloride

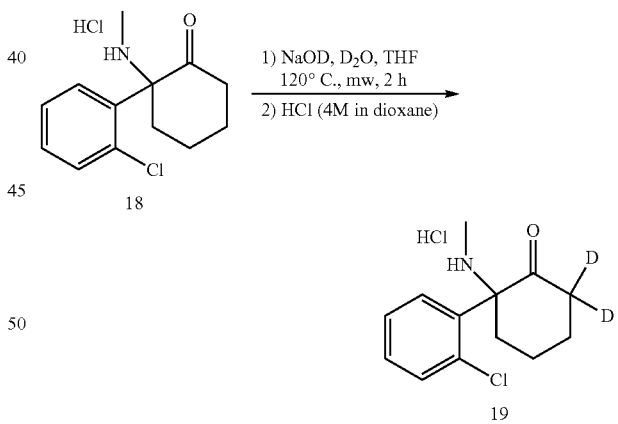

In an embodiment, a synthesis shown above in Scheme 7 for (2S,6S)-hydroxynorketamine begins with a chiral resolution of racemic norketamine 13, which separates racemic norketamine into (S)-norketamine 14 and its enantiomer (R)-norketamine. This can be accomplished by use of a chiral resolving agent, such as D-tartaric acid, or by other methods, which may include chromatography on a chiral medium such as a chiral HPLC column. Alternatively, homochiral or enantioenriched norketamine can be obtained by an enantioselective synthetic method. The subsequent steps of Scheme 1 can be applied to (S)-norketamine 13 to eventually produce (2S,6S)-hydroxynorketamine 17, or the steps can be applied to (R)-norketamine to eventually produce (2R,6R)-hydroxynorketamine.

In Scheme 6 (S)-norketamine 14 is reacted with di-tert-butyl-dicarbonate in the presence of potassium carbonate in toluene at 80° C. to produce the Boc-protected compound 15.

Further in Scheme 6, compound 15 in THF at −78° C. is treated with lithium diisopropylamide and trimethylsilyl chloride to produce an intermediate which is believed to be enol ether 16, but is used in the next reaction without characterization. While not wanting to be bound by theory, it is believed that the lithium diisopropylamide removes a proton alpha to the carbonyl of compound 15, generating an enolate, and the enolate then reacts on its oxygen atom with trimethylsilyl chloride to generate the silyl enol ether 16.

Following the removal of the proton alpha to the carbonyl of 15, trimethylsilylchloride is added to react with the enolate produced from 15.

In Scheme 6, once intermediate 16 is formed, it is treated with m-peroxybenzoic acid (mCPBA) and then a fluoride source to provide compound 8, which is Boc-protected (2S,6S)-hydroxynorketamine.

While not wanting to be bound by theory, the mCPBA treatment is believed to generate an alpha-siloxyepoxide, and the fluoride treatment cleaves the silicon oxygen bond to produce an alpha-hydroxyepoxide, which then ring opens to provide alpha-hydroxyketone 8.

In Scheme 6, compound 8 is treated with trifluoroacetic acid to remove the Boc group and thus deprotect the 2-amino group of (2S,6S)-hydroxynorketamine. The resulting salt is then converted to the free base using sodium bicarbonate. The resulting free base is then treated with hydrochloric acid to produce the (2S,6S)-hydroxynorketamine hydrochloride salt 17. Other acids can be used to make other salts of (2S,6S)-hydroxynorketamine.

EXAMPLES

General Methods
Chemical Methods

All commercially available reagents and solvents were purchased and used without further purification. All microwave reactions were carried out in a sealed microwave vial equipped with a magnetic stir bar and heated in a Biotage Initiator Microwave Synthesizer. $^1$H NMR and $^{13}$C NMR spectra were recorded on Varian 400 MHz or Varian 600 MHz spectrometers in CD$_3$OD or CDCl$_3$ as indicated. For spectra recorded in CD$_3$OD, chemical shifts are reported in ppm with CD$_3$OD (3.31 MHz) as reference for $^1$H NMR spectra and CD$_3$OD (49.0 MHz) for $^{13}$C NMR spectra. Alternatively for spectra recorded in CDCl$_3$, chemical shifts are reported in ppm relative to deuterochloroform (7.26 ppm for $^1$H NMR, 77.23 ppm for $^{13}$C NMR. The coupling constants (J value) are reported as Hertz (Hz). The splitting patterns of the peaks were described as: singlet (s); doublet (d); triplet (t); quartet (q); multiplet (m) and septet (septet). Samples were analyzed for purity on an Agilent 1200 series LC/MS equipped with a Luna C$_{18}$ (3 mm×75 mm, 3 µm) reversed-phase column with UV detection at X=220 nm and X=254 nm. The mobile phase consisted of water containing 0.05% trifluoroacetic acid as component A and acetonitrile containing 0.025% trifluoroacetic acid as component B. A linear gradient was run as follows: 0 min 4% B; 7 min 100% B; 8 min 100% B at a flow rate of 0.8 mL/min. High resolution mass spectrometry (HRMS) was recorded on Agilent 6210 Time-of-Flight (TOF) LC/MS system. Optical rotations were measured on a PerkinElmer model 341 polarimeter using a 10 cm cell, at 589 nM and room temperature.

Chiral analysis was carried out with an Agilent 1200 series HPLC using an analytical Chiralpak AD or OJ column (4.6 mm×250 mm; 5 µm). The mobile phase consisted of ethanol containing 0.1% diethylamine as component A and hexanes containing 0.1% diethylamine as component B. An isocratic gradient was run at 0.4 mL/min with 60% A.

(2R,6R)-hydroxynorketamine hydrochloride and (2S,6S)-hydroxynorketamine are previously described in US 2014/0296241. The synthesis and crystalline forms disclosed herein have not been previously described.

EXAMPLES

Example 1. Chiral Resolution of (S)-(+)-Norketamine (14)

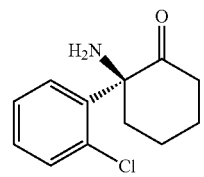

(14)

Racemic norketamine (22.7 grams, 101 mmol) (Cayman Chemicals, Ann Arbor, Mich., USA, prepared as described in Hong, S. C.& Davisson, J. N., *J. Pharm. Sci.* (1982) 71: 912-914) was dissolved in 1.1 L ethanol. Then (D)-(R)-(+)-pyroglutamic acid (15.8 g, 0.5 eq., 121 mmol) was added as a solid. The reaction was stirred and heated to reflux for 5 minutes. While heating, a white suspension formed. Once the suspension reached reflux, it was allowed to cool to room temperature while stirring for 16 hours. The reaction was filtered and the white solid was collected. The resulting white solid was then resuspended in 0.9 L of ethanol and the suspension was heated to reflux for 5 minutes. The suspension was allowed to cool to room temperature over 2 hours while stirring. The solid was collected by filtration, then suspended a third time in ethanol (0.8 L), heated to reflux for 5 minutes, then allowed to cool to room temperature while stirring. The solid was filtered, collected and dried under vacuum to give (S)-(+)-norketamine D-pyroglutamate. The enantiomeric excess measured by chiral HPLC to give an enantiomeric excess of 98.3%. The (S)-(+)-norketamine D-pyroglutamate salt was converted to the free base by treatment with 1 N aqueous sodium hydroxide, extraction into ethyl acetate, and removal of the organic solvent by rotary evaporation to provide (S)-(+)-norketamine as the free base (from the pyroglutamate salt). (Chiralpak AD column, 60% ethanol in hexanes with 0.01% diethylamine, 1.0 mL, rt: 5.2 min) $[\alpha]_D^{20}$: (+) 81° (c 1.0, H$_2$O, D-pyroglutamate salt).

Example 2. Chiral Resolution of (R)-(−)-Norketamine (14a)

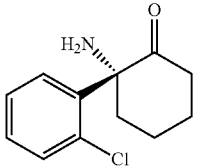

(14A)

(R)-(−)-Norketamine (14A) was produced in an analogous fashion to that of (S)-(+)-norketamine (2), except that (L)-(S)-(−)-pyroglutamic acid was used as a chiral resolution agent instead of (D)-(R)-(+)-pyroglutamic acid Chiral HPLC: 98% ee. (Chiralpak AD, 60% ethanol in hexanes, 1 mL/min, rt: 6.8 min.) $[\alpha]_D^{20}$: (−)−75° (c 1.0, $H_2O$, L-pyroglutamate salt).

Example 3. Synthesis of (S)-tert-Butyl (1-(2-chlorophenyl)-2-oxocyclohexyl)carbamate (15)

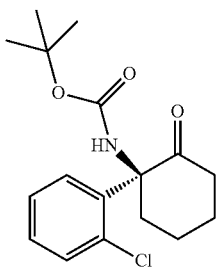

(15)

To a solution of (S)-(+)-norketamine (14) (1.85 g, 8.27 mmol) in toluene (100 mL) was added potassium carbonate (3.43 g, 24.8 mmol) and BOC-anhydride (2.71 g, 12.4 mmol). The reaction was heated to 80° C. and stirred for 16 hours. The reaction was then cooled, extracted with ethyl acetate and washed with water. The organic layer was taken and the solvent removed in vacuo to give the crude product. Purification by silica gel chromatography (0% to 60% ethyl acetate in hexanes) gave the final product (15) as a white solid.

$^1$H NMR (400 MHz, $CDCl_3$) δ 7.83 (d, J=8.0 Hz, 1H), 7.42-7.28 (m, 2H), 7.28-7.13 (m, 1H), 6.59 (s, 1H), 3.83 (d, J=14.3 Hz, 1H), 2.45-2.36 (m, 1H), 2.36-2.25 (m, 1H), 2.04 (ddq, J=11.5, 5.5, 3.0 Hz, 1H), 1.89-1.56 (m, 4H), 1.29 (s, 9H).

$^{13}$C NMR (101 MHz, $CDCl_3$) δ 209.0, 153.4, 135.1, 133.7, 131.5, 130.9, 129.2, 126.2, 79.0, 67.1, 39.4, 38.4, 30.8, 28.2, 22.3.

HRMS (ESI+): Expected 346.1186 [M+Na] ($C_{17}H_{22}ClNO_3Na$). Observed 346.1180. $[\alpha]_D^{20}$: (+)−39.5° (c1.0, $CH_2Cl_2$).

Example 4. Synthesis of (R)-tert-Butyl (1-(2-chlorophenyl)-2-oxocyclohexyl)carbamate (15a)

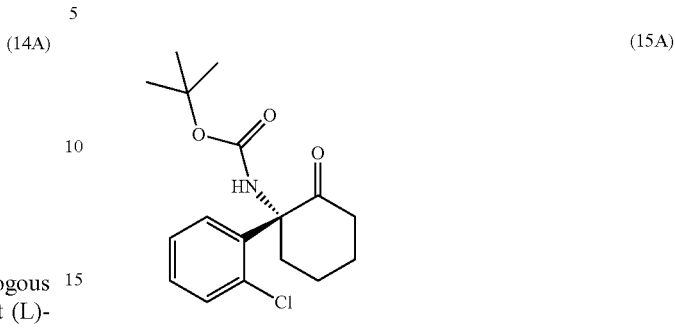

(15A)

The title compound was prepared in an analogous fashion to (S)-tert-butyl (1-(2-chlorophenyl)-2-oxocyclohexyl)carbamate (15), utilizing (R)-(−)-norketamine (14A) instead of (S)-(+)-norketamine (14).

$^1$H NMR (400 MHz, $CDCl_3$) δ 7.85 (d, J=8.0 Hz, 1H), 7.34 (dd, J=8.0, 1.4 Hz, 2H), 7.30-7.21 (m, 1H), 6.61 (s, 1H), 3.84 (d, J=14.4 Hz, 1H), 2.47-2.37 (m, 1H), 2.38-2.29 (m, 1H), 2.09-2.02 (m, 1H), 1.86-1.62 (m, 4H), 1.31 (s, 9H).

$^{13}$C NMR (101 MHz, $CDCl_3$) δ 209.0, 153.4, 135.0, 133.7, 131.5, 130.8, 129.2, 126.2, 79.0, 67.1, 39.4, 38.4, 30.8, 28.2, 22.3.

HRMS (ESI+): Expected 346.1186 [M+Na] ($C_{17}H_{22}ClNO_3Na$). Observed 346.1188. $[\alpha]_D^{20}$: (−)−60.7° (c 1.0, $CH_2Cl_2$).

Example 5. Synthesis of tert-Butyl ((1S,3S)-1-(2-chlorophenyl)-3-hydroxy-2-oxocyclohexyl)carbamate (8)

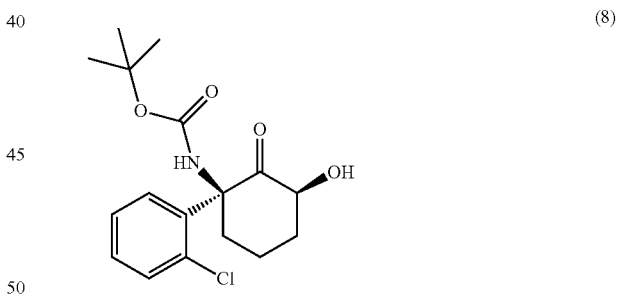

(8)

A solution of (S)-tert-butyl (1-(2-chlorophenyl)-2-oxocyclohexyl)carbamate 15 (6.5 grams) in THF (100 mL), was cooled to −78° C. under a nitrogen atmosphere. Lithium diisopropylamide (2.0 M in THF/heptane/ethylbenzene, 26 mL, 2.6 eq.) was added by syringe. The reaction was stirred 1 hour at −78° C., then allowed to warm to room temperature for 5 minutes. The reaction was cooled to −78° C., and chlorotrimethylsilane (5.7 grams, 2.6 eq.) was added as a neat liquid by syringe. The reaction was stirred for 30 minutes at −78° C., and then allowed to warm to room temperature over 30 minutes. The reaction was then quenched by being poured into aqueous saturated ammonium chloride. Ethyl acetate was added to the resulting mixture, the organic phase was separated and the solvent was removed by rotary evaporation to give the crude enol ether 16 as a solid which was immediately used without further purification. The enol ether 16 (7.8 grams) was dissolved in dichloromethane (100 mL) and cooled to −15° C. (ice-lithium chloride), under a nitrogen atmosphere. 3-Chloroperbenzoic acid (5.0 grams, 1.1 eq.) was then added as a solid. The reaction was stirred for one hour at −15° C., then the temperature was raised to room temperature and an additional 100 mL of dichloromethane was added. The reaction was stirred a further 0.5 hours. The reaction was then quenched by being poured into a 50/50 mixture of saturated aqueous sodium thiosulfate and saturated aqueous sodium bicarbonate. The reaction was extracted into dichloromethane and the solvent removed by rotary evaporation. Then tetrahydrofuran (100 mL) was added to the crude material. The reaction was cooled to −5° C., and tetra-n-butylbutyl ammonium fluoride (1.0 M in THF, 25 mL, 1.2 eq. was added). The reaction was stirred for 2 minutes, before being quenched by addition to saturated aqueous sodium bicarbonate. Extraction into ethyl acetate, followed by removal of the solvent by rotary evaporation gave the crude final product 8. Purification by silica gel chromatography (0% to 70% ethyl acetate in hexanes), gave the purified final product as a solid.

$^1$H NMR (400 MHz, CDCl$_3$) δ 7.80 (d, J=7.9 Hz, 1H), 7.34 (ddd, J=8.8, 7.1, 1.4 Hz, 2H), 7.29-7.18 (m, 1H), 6.60 (s, 1H), 4.12 (dd, J=11.8, 6.7 Hz, 1H), 3.87 (d, J=14.3 Hz, 1H), 3.38 (s, 1H), 2.36 (ddq, J=13.1, 6.5, 3.2 Hz, 1H), 1.74 (ddt, J=7.8, 5.7, 2.8 Hz, 2H), 1.69-1.59 (m, 1H), 1.59-1.40 (m, 1H), 1.30 (s, 9H).

$^{13}$C NMR (101 MHz, CDCl$_3$) δ 209.9, 153.3, 134.1, 133.8, 131.4, 131.0, 129.7, 126.3, 79.4, 72.4, 66.7, 40.4, 38.8, 28.2, 19.6.

HRMS (ESI+): Expected 362.1135 [M+Na] (C$_{17}$H$_{22}$ClNO$_4$Na). Observed 362.1134. [α]$_D^{20}$: (+)−60.7° (c1.0, CHCl$_3$).

Example 6. Synthesis of tert-Butyl ((1R,3R)-1-(2-chlorophenyl)-3-hydroxy-2-oxocyclohexyl)carbamate (8a)

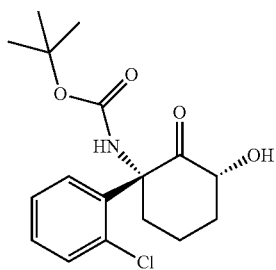

(8A)

The title compound was prepared in an analogous fashion to (tert-butyl ((1S,3S)-1-(2-chlorophenyl)-3-hydroxy-2-oxocyclohexyl)carbamate 5 by utilizing (R)-tert-butyl (1-(2-chlorophenyl)-2-oxocyclohexyl)carbamate instead of the S-enantiomer.

$^1$H NMR (400 MHz, CDCl$_3$) δ 7.80 (d, J=7.9 Hz, 1H), 7.34 (dd, J=8.5, 6.9 Hz, 2H), 7.32-7.21 (m, 1H), 6.60 (s, 1H), 4.12 (ddd, J=11.5, 8.9, 6.3 Hz, 1H), 3.92-3.83 (m, 1H), 3.37 (d, J=6.5 Hz, 1H), 2.36 (ddq, J=13.0, 6.5, 3.2 Hz, 1H), 1.74 (dq, J=6.4, 3.2, 2.5 Hz, 2H), 1.63 (dq, J=16.8, 9.2, 8.2 Hz, 1H), 1.59-1.40 (m, 1H), 1.30 (s, 9H).

$^{13}$C NMR (101 MHz, CDCl$_3$) δ 209.9, 153.3, 134.1, 133.8, 131.4, 131.0, 129.7, 126.3, 79.4, 72.4, 66.7, 40.4, 38.8, 28.2, 19.5.

HRMS (ESI+): Expected 362.1135 [M+Na] (C$_{17}$H$_{22}$ClNO$_4$Na). Observed 362.1134. [α]$_D^{20}$: (−)−63.7° (c 1.0, CHCl$_3$).

Example 7. Synthesis of (2S,6S)-(+)-2-amino-2-(2-chlorophenyl)-6-hydroxycyclohexanone hydrochloride ((2S,6S)-(+)-Hydroxynorketamine hydrochloride) (17)

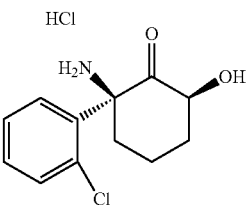

(17)

To a solution of tert-butyl ((1S,3S)-1-(2-chlorophenyl)-3-hydroxy-2-oxocyclohexyl)carbamate 8 (4.85 grams) in dichloromethane (10 mL) was added trifluoroacetic acid (11.0 mL, 10 eq.). The reaction was stirred at room temperature for 1 hour. The solvent and trifluoroacetic acid (TFA) were then removed by rotary evaporation. The resulting TFA salt was dissolved in water, washed with a 50/50 mixture of saturated aqueous sodium bicarbonate and saturated aqueous potassium carbonate solution, and extracted with ethyl acetate (2×) to give the free base. The ethyl acetate was removed by rotary evaporation. Ethyl acetate (4 mL) was added and HCl in dioxane (4.0 M, 6.0 mL) was added. A white solid crashed out. The suspension was agitated for 30 seconds and then the solid was filtered off and dried under vacuum to give the desired final product (17).

$^1$H NMR (400 MHz, MeOD) δ 7.92-7.81 (m, 1H), 7.66-7.50 (m, 3H), 4.28 (dd, J=11.7, 6.6 Hz, 1H), 3.19 (dd, J=14.0, 3.0 Hz, 1H), 2.30 (dddd, J=12.2, 6.6, 4.1, 2.3 Hz, 1H), 1.80-1.70 (m, 2H), 1.68-1.52 (m, 2H).

$^{13}$C NMR (100 MHz, MeOD): δ 206.8, 134.0, 132.1, 131.6, 130.5, 130.0, 128.3, 73.0, 67.0, 38.4, 37.1, 18.7.

Chiral HPLC: 98.3% ee (Chiralpak AD column, 60% ethanol in hexanes, 1.0 mL/min, rt=6.0 min.)

HRMS (ESI+): Expected 240.0786 [M+H] (C$_{12}$H$_{15}$ClNO$_2$). Observed 240.0782. [α]$_D^{20}$: (+) 95° (c 1.0, H$_2$O).

Example 8. Synthesis of (2R,6R)-(−)-2-amino-2-(2-chlorophenyl)-6-hydroxycyclohexanone hydrochloride (17a) ((2R,6R)-(−)-hydroxynorketamine hydrochloride)

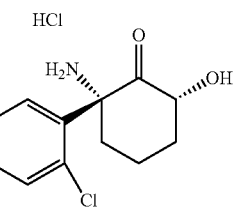

(17A)

The title compound was prepared in an analogous fashion to that of (2S,6S)-(+)-hydroxynorketamine hydrochloride by utilizing tert-butyl ((1R,3R)-1-(2-chlorophenyl)-3-hydroxy-2-oxocyclohexyl)carbamate (17A) instead of the S,S-enantiomer.

$^1$H NMR (400 MHz, MeOD): δ 7.94-7.83 (m, 1H), 7.62-7.53 (m, 3H), 4.29 (dd, =11.6, 6.7 Hz, 1H), 3.19 (dd, J=14.0, 3.0 Hz, 1H), 2.30 (dddd, J=12.2, 6.6, 4.1, 2.3 Hz, 1H), 1.99-1.82 (m, 2H), 1.82-1.56 (m, 2H)

$^{13}$C NMR (100 MHz, MeOD): δ 206.8, 134.0, 132.1, 131.6, 130.5, 130.1, 128.3, 73.3, 67.0, 38.4, 37.2, 18.7

Chiral HPLC: 98.3% ee (Chiralpak AD column, 60% ethanol in hexanes, 1.0 mL/min, rt=7.9 min)

HRMS (ESI+): Expected 262.0605 [M+Na] ($C_{12}H_{14}ClNO_2Na$). Observed 262.0605 $[α]_D^{20}$: (−)−92° (c 1.0, $H_2O$).

Example 9. Synthesis of 6,6-dideuteroketamine hydrochloride (19)

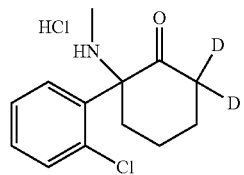

(19)

Sodium deuteroxide (30% in deuterium oxide, 3.0 mL) was added to a solution of racemic ketamine hydrochloride (0.80 grams, 2.9 mmol) in a mixture of tetrahydrofuran (8.0 mL) and deuterium oxide (3.0 mL). The reaction was heated by microwave irradiation in a sealed vial to 120° C. for 2 hours. The reaction was cooled, extracted with ethyl acetate and washed with saturated aqueous sodium bicarbonate. The organic phase was taken and the solvent removed by rotary evaporation to give the crude product. Purification by reverse phase liquid chromatography (5% to 95% acetonitrile in water with 0.1% trifluoroacetic acid) gave the purified TFA salt. The free base was formed and isolated by washing the TFA salt with saturated aqueous sodium bicarbonate and extraction with ethyl acetate. The HCl salt was formed by the addition of HCl (4.0 M in dioxane), and filtration of the resulting white solid, to provide the title compound as a white solid.

$^1$H NMR (400 MHz, MeOD): δ 7.94-7.88 (m, 1H), 7.66-7.57 (m, 3H), 3.41-3.34 (m, 1H), 2.38 (s, 3H), 2.27-2.20 (m, 1H), 1.93-1.83 (m, 2H), 1.83-1.69 (m, 2H).

$^{13}$C NMR (600 MHz, MeOD): δ 208.6, 136.1, 134.1, 133.6, 133.5, 129.9, 129.4, 73.8, 40.3 (septet, $J_{C-D}$=21 Hz, 1C), 37.6, 31.2, 28.1, 23.0.

HRMS (ESI+): Expected 240.1119 [M+H], ($C_{13}H_{15}D_2ClN_O$). Observed 240.1120.

Example 10. X-ray crystallography of (2S,6S)-(+)-hydroxynorketamine hydrochloride The single crystal X-ray diffraction studies were carried out on a Bruker Kappa APEX-II CCD diffractometer equipped with Mo $K_α$ radiation (λ=0.71073 Å). Crystals of the subject compound were grown by slow evaporation of a 50/50 Dichloroethane/Methanol solution. A 0.227×0.215×0.106 mm piece of a colorless block was mounted on a Cryoloop with Paratone oil. Data were collected in a nitrogen gas stream at 100(2) K using φ and ω̄ scans. Crystal-to-detector distance was 40 mm and exposure time was 5 seconds per frame using a scan width of 2.0°. Data collection was 100% complete to 25.00° in θ. A total of 9466 reflections were collected covering the indices, −9<=h<=9, −9<=k<=9, −14<=l<=14. 2949 reflections were found to be symmetry independent, with a $R_{int}$ of 0.0376. Indexing and unit cell refinement indicated a primitive, monoclinic lattice. The space group was found to be P2$_1$. The data were integrated using the Bruker SAINT software program and scaled using the SADABS software program. Solution by direct methods (SHELXT) produced a complete phasing model consistent with the proposed structure.

All nonhydrogen atoms were refined anisotropically by full-matrix least-squares (SHELXL-2014). All carbon bonded hydrogen atoms were placed using a riding model. Their positions were constrained relative to their parent atom using the appropriate HFIX command in SHELXL-2014. All other hydrogen atoms (H-bonding) were located in the difference map. Their relative positions were restrained using DFIX commands and their thermals freely refined. The absolute stereochemistry of the molecule was established by anomalous dispersion using the Parson's method with a Flack parameter of −0.001. A depiction of the crystal structure is shown in FIG. 1. Crystallographic data are summarized in Tables 1-6.

TABLE 1

Crystal data and structure refinement for (2S,6S)-hydroxynorketamine hydrochloride

| Property | Result |
| --- | --- |
| Temperature | 100.0 K |
| Wavelength | 0.71073 Å |
| Crystal system | Monoclinic |
| Space group | P 1 21 1 |
| Unit cell dimensions | a = 7.3493(8) Å α = 90°. |
| | b = 7.4846(8) Å β = 96.866(3)°. |
| | c = 11.3404(12) Å γ = 90°. |
| Volume | 619.32(12) Å$^3$ |
| Z | 2 |
| Density (calculated) | 1.481 Mg/m$^3$ |
| Absorption coefficient | 0.513 mm$^{-1}$ |
| F(000) | 288 |
| Crystal size | 0.227 × 0.215 × 0.106 mm$^3$ |
| Crystal color, habit | Colorless Block |
| Theta range for data collection | 1.809 to 28.411° |
| Index ranges | −9 <= h <= 9, −9 <= k <= 9, −14 <= l <= 14 |
| Reflections collected | 9466 |
| Independent reflections | 2949 [R(int) = 0.0376] |
| Completeness to theta = 25.000° | 100.0% |
| Absorption correction | Semi-empirical from equivalents |
| Max. and min. transmission | 0.0962 and 0.0677 |
| Refinement method | Full-matrix least-squares on F$^2$ |
| Data/restraints/parameters | 2949/5/170 |
| Goodness-of-fit on F$^2$ | 1.075 |
| Final R indices [I > 2sigma(I)] | R1 = 0.0239, wR2 = 0.0624 |
| R indices (all data) | R1 = 0.0245, wR2 = 0.0629 |
| Absolute structure parameter | 0.00(2) |
| Extinction coefficient | n/a |
| Largest diff. peak and hole | 0.287 and −0.204 e.Å$^{-3}$ |

TABLE 2

Atomic coordinates (×10⁴) and equivalent isotropic displacement parameters ($\text{Å}^2 \times 10^3$) for (2S,6S)-hydroxynorketamine hydrochloride. U(eq) is defined as one third of the trace of the orthogonalized $U^{ij}$ tensor.

|       | x        | y        | z        | U(eq) |
|-------|----------|----------|----------|-------|
| Cl(1) | 6563(1)  | 1930(1)  | 1363(1)  | 22(1) |
| O(1)  | 5226(2)  | 2952(2)  | 3850(1)  | 19(1) |
| O(2)  | 1922(2)  | 4022(2)  | 2743(1)  | 19(1) |
| N(1)  | 8564(2)  | 4290(2)  | 3690(2)  | 16(1) |
| C(1)  | 5225(2)  | 4235(3)  | 3197(2)  | 15(1) |
| C(2)  | 3480(2)  | 5092(2)  | 2626(2)  | 16(1) |
| C(3)  | 3299(3)  | 6901(3)  | 3233(2)  | 18(1) |
| C(4)  | 4997(3)  | 8055(3)  | 3174(2)  | 19(1) |
| C(5)  | 6740(2)  | 7066(3)  | 3678(2)  | 17(1) |
| C(6)  | 6981(2)  | 5272(3)  | 3034(2)  | 14(1) |
| C(7)  | 7326(2)  | 5480(3)  | 1734(2)  | 15(1) |
| C(8)  | 7195(3)  | 4052(3)  | 939(2)   | 17(1) |
| C(9)  | 7583(3)  | 4231(3)  | −224(2)  | 21(1) |
| C(10) | 8130(3)  | 5875(3)  | −621(2)  | 24(1) |
| C(11) | 8284(3)  | 7311(3)  | 146(2)   | 23(1) |
| C(12) | 7907(3)  | 7117(3)  | 1311(2)  | 19(1) |
| Cl(2) | 376(1)   | 481(1)   | 3708(1)  | 18(1) |

TABLE 3

Bond lengths [Å] and angles [°] for (2S,6S)-hydroxynorketamine hydrochloride

| Bond | Bond Length (Å) | Bonds in Angle | Bond Angle (°) |
|------|-----------------|----------------|----------------|
| Cl(1)—C(8) | 1.739(2) | C(2)—O(2)—H(2) | 113(2) |
| O(1)—C(1) | 1.213(3) | H(1A)—N(1)—H(1B) | 105(2) |
| O(2)—H(2) | 0.90(2) | H(1A)—N(1)—H(1C) | 109(2) |
| O(2)—C(2) | 1.417(2) | H(1B)—N(1)—H(1C) | 103(2) |
| N(1)—H(1A) | 0.937(19) | C(6)—N(1)—H(1A) | 110.7(17) |
| N(1)—H(1B) | 0.93(2) | C(6)—N(1)—H(1B) | 115.3(16) |
| N(1)—H(1C) | 0.94(2) | C(6)—N(1)—H(1C) | 112.4(16) |
| N(1)—C(6) | 1.496(2) | O(1)—C(1)—C(2) | 122.48(16) |
| C(1)—C(2) | 1.509(3) | O(1)—C(1)—C(6) | 122.31(18) |
| C(1)—C(6) | 1.536(2) | C(2)—C(1)—C(6) | 114.63(16) |
| C(2)—H(2A) | 1.0000 | O(2)—C(2)—C(1) | 112.02(15) |
| C(2)—C(3) | 1.532(3) | O(2)—C(2)—H(2A) | 109.1 |
| C(3)—H(3A) | 0.9900 | O(2)—C(2)—C(3) | 110.04(15) |
| C(3)—H(3B) | 0.9900 | C(1)—C(2)—H(2A) | 109.1 |
| C(3)—C(4) | 1.526(3) | C(1)—C(2)—C(3) | 107.38(16) |
| C(4)—H(4A) | 0.9900 | C(3)—C(2)—H(2A) | 109.1 |
| C(4)—H(4B) | 0.9900 | C(2)—C(3)—H(3A) | 109.3 |
| C(4)—C(5) | 1.529(3) | C(2)—C(3)—H(3B) | 109.3 |
| C(5)—H(5A) | 0.9900 | H(3A)—C(3)—H(3B) | 108.0 |
| C(5)—H(5B) | 0.9900 | C(4)—C(3)—C(2) | 111.40(15) |
| C(5)—C(6) | 1.548(3) | C(4)—C(3)—H(3A) | 109.3 |
| C(6)—C(7) | 1.534(3) | C(4)—C(3)—H(3B) | 109.3 |
| C(7)—C(8) | 1.394(3) | C(3)—C(4)—H(4B) | 109.4 |
| C(7)—C(12) | 1.401(3) | C(3)—C(4)—C(5) | 111.26(16) |
| C(8)—C(9) | 1.389(3) | H(4A)—C(4)—H(4B) | 108.0 |
| C(9)—H(9) | 0.9500 | C(5)—C(4)—H(4A) | 109.4 |
| C(9)—C(10) | 1.386(3) | C(5)—C(4)—H(4B) | 109.4 |
| C(10)—H(10) | 0.9500 | C(4)—C(5)—H(5A) | 109.1 |
| C(10)—C(11) | 1.379(3) | C(4)—C(5)—H(5B) | 109.1 |
| C(11)—H(11) | 0.9500 | C(4)—C(5)—C(6) | 112.43(16) |
| C(11)—C(12) | 1.389(3) | H(5A)—C(5)—H(5B) | 107.8 |
| C(12)—H(12) | 0.9500 | C(6)—C(5)—H(5A) | 109.1 |
| | | C(6)—C(5)—H(5B) | 109.1 |
| | | N(1)—C(6)—C(1) | 107.84(15) |
| | | N(1)—C(6)—C(5) | 108.54(15) |
| | | N(1)—C(6)—C(7) | 108.62(14) |
| | | C(1)—C(6)—C(5) | 103.68(14) |
| | | C(7)—C(6)—C(1) | 113.84(15) |
| | | C(7)—C(6)—C(5) | 114.01(16) |
| | | C(8)—C(7)—C(6) | 122.52(18) |
| | | C(8)—C(7)—C(12) | 116.72(18) |
| | | C(12)—C(7)—C(6) | 120.65(18) |
| | | C(7)—C(8)—Cl(1) | 121.42(15) |
| | | C(9)—C(8)—Cl(1) | 116.29(17) |
| | | C(9)—C(8)—C(7) | 122.29(19) |
| | | C(8)—C(9)—H(9) | 120.2 |
| | | C(10)—C(9)—C(8) | 119.6(2) |
| | | C(10)—C(9)—H(9) | 120.2 |
| | | C(9)—C(10)—H(10) | 120.3 |
| | | C(11)—C(10)—C(9) | 119.47(19) |
| | | C(11)—C(10)—H(10) | 120.3 |
| | | C(10)—C(11)—H(11) | 119.7 |
| | | C(10)—C(11)—C(12) | 120.5(2) |
| | | C(12)—C(11)—H(11) | 119.7 |
| | | C(7)—C(12)—H(12) | 119.3 |
| | | C(11)—C(12)—C(7) | 121.4(2) |
| | | C(11)—C(12)—H(12) | 119.3 |

TABLE 4

Anisotropic displacement parameters ($\text{Å}^2 \times 10^3$) for (2S,6S)-hydroxynorketamine hydrochloride. The anisotropic displacement factor exponent takes the form: $-2\pi^2[h^2 a^{*2} U^{11} + \ldots + 2 h k a^* b^* U^{12}]$

|       | $U^{11}$ | $U^{22}$ | $U^{33}$ | $U^{23}$ | $U^{13}$ | $U^{12}$ |
|-------|------|------|------|-------|------|-------|
| Cl(1) | 27(1) | 16(1) | 22(1) | −3(1) | 3(1) | −2(1) |
| O(1)  | 19(1) | 18(1) | 21(1) | 3(1) | 5(1) | 0(1) |
| O(2)  | 13(1) | 20(1) | 23(1) | 2(1) | 3(1) | −1(1) |
| N(1)  | 14(1) | 18(1) | 15(1) | 0(1) | 2(1) | 1(1) |
| C(1)  | 16(1) | 15(1) | 14(1) | −4(1) | 4(1) | 1(1) |
| C(2)  | 14(1) | 16(1) | 18(1) | 1(1) | 3(1) | −1(1) |
| C(3)  | 17(1) | 17(1) | 21(1) | −2(1) | 3(1) | 4(1) |
| C(4)  | 20(1) | 15(1) | 22(1) | −1(1) | 2(1) | 1(1) |
| C(5)  | 18(1) | 15(1) | 18(1) | −2(1) | 1(1) | 1(1) |
| C(6)  | 13(1) | 14(1) | 15(1) | −1(1) | 2(1) | 1(1) |
| C(7)  | 12(1) | 18(1) | 16(1) | 2(1) | 1(1) | 2(1) |
| C(8)  | 15(1) | 18(1) | 18(1) | 1(1) | 1(1) | 1(1) |
| C(9)  | 19(1) | 28(1) | 16(1) | −2(1) | 1(1) | 4(1) |
| C(10) | 21(1) | 35(1) | 17(1) | 7(1) | 3(1) | 5(1) |
| C(11) | 18(1) | 27(1) | 24(1) | 8(1) | 4(1) | 1(1) |
| C(12) | 16(1) | 20(1) | 21(1) | 2(1) | 2(1) | −2(1) |
| Cl(2) | 20(1) | 16(1) | 18(1) | 0(1) | 1(1) | 1(1) |

TABLE 5

Hydrogen coordinates (×10⁴) and isotropic displacement parameters ($\text{Å}^2 \times 10^3$) for (2S,6S)-hydroxynorketamine hydrochloride.

|       | x       | y       | z       | U(eq) |
|-------|---------|---------|---------|-------|
| H(2)  | 2200(40) | 3010(30) | 3160(30) | 40(9) |
| H(1A) | 9650(30) | 4530(40) | 3360(20) | 23(6) |
| H(1B) | 8460(30) | 3060(30) | 3690(20) | 19(6) |
| H(1C) | 8730(40) | 4570(40) | 4506(19) | 23(6) |
| H(2A) | 3575 | 5291 | 1764 | 19 |
| H(3A) | 2209 | 7535 | 2840 | 22 |
| H(3B) | 3116 | 6706 | 4074 | 22 |
| H(4A) | 4882 | 9168 | 3631 | 23 |
| H(4B) | 5086 | 8387 | 2338 | 23 |
| H(5A) | 6695 | 6831 | 4533 | 20 |
| H(5B) | 7815 | 7836 | 3604 | 20 |
| H(9)  | 7474 | 3232 | −745 | 25 |
| H(10) | 8397 | 6012 | −1416 | 29 |
| H(11) | 8650 | 8442 | −124 | 27 |
| H(12) | 8047 | 8115 | 1832 | 23 |

TABLE 6

Hydrogen bonds for (2S,6S)-hydroxynorketamine hydrochloride [Å and °]

| D-H . . . A | d(D-H) | d(H . . . A) | d(D . . . A) | <(DHA) |
|---|---|---|---|---|
| O(2)—H(2) . . . Cl(2) | 0.90(2) | 2.44(3) | 3.1317(16) | 133(3) |
| N(1)—H(1A) . . . O(2)#1 | 0.937(19) | 1.92(2) | 2.814(2) | 158(2) |
| N(1)—H(1B) . . . Cl(2)#1 | 0.93(2) | 2.39(2) | 3.1460(19) | 139(2) |
| N(1)—H(1C) . . . Cl(2)#2 | 0.94(2) | 2.16(2) | 3.0925(18) | 168(2) |

Symmetry transformations used to generate equivalent atoms:
1 x + 1, y, z
2 −x + 1, y + ½, −z + 1

Example 11. X-Ray Crystallography of (2R,6R)-Hydroxynorketamine Hydrochloride The single crystal X-ray diffraction studies were carried out on a Bruker Kappa APEX-II CCD diffractometer equipped with Mo K$_\alpha$ radiation ($\lambda$=0.71073 Å). Crystals of the subject compound were grown by slow evaporation of an isopropanol solution. A 0.157×0.131×0.098 mm piece of a colorless block was mounted on a Cryoloop with Paratone oil. Data were collected in a nitrogen gas stream at 100(2) K using A 0.157×0.131×0.098 mm piece of a colorless block was mounted on a Cryoloop with Paratone oil. Data were collected in a nitrogen gas stream at 100(2) K using $\phi$ and $\omega$ scans. Crystal-to-detector distance was 40 mm and exposure time was 3 seconds per frame using a scan width of 2.0°. Data collection was 100% complete to 25.00° in θ. A total of 7618 reflections were collected covering the indices, −9<=h<=9, −9<=k<=9, −14<=l<=14. 2927 reflections were found to be symmetry independent, with a R$_{int}$ of 0.0350. Indexing and unit cell refinement indicated a primitive, monoclinic lattice. The space group was found to be P2$_1$. The data were integrated using the Bruker SAINT software program and scaled using the SADABS software program. Solution by direct methods (SHELXT) produced a complete phasing model consistent with the proposed structure.

All nonhydrogen atoms were refined anisotropically by full-matrix least-squares (SHELXL-2014). All carbon bonded hydrogen atoms were placed using a riding model. Their positions were constrained relative to their parent atom using the appropriate HFIX command in SHELXL-2014.

Figure 2:
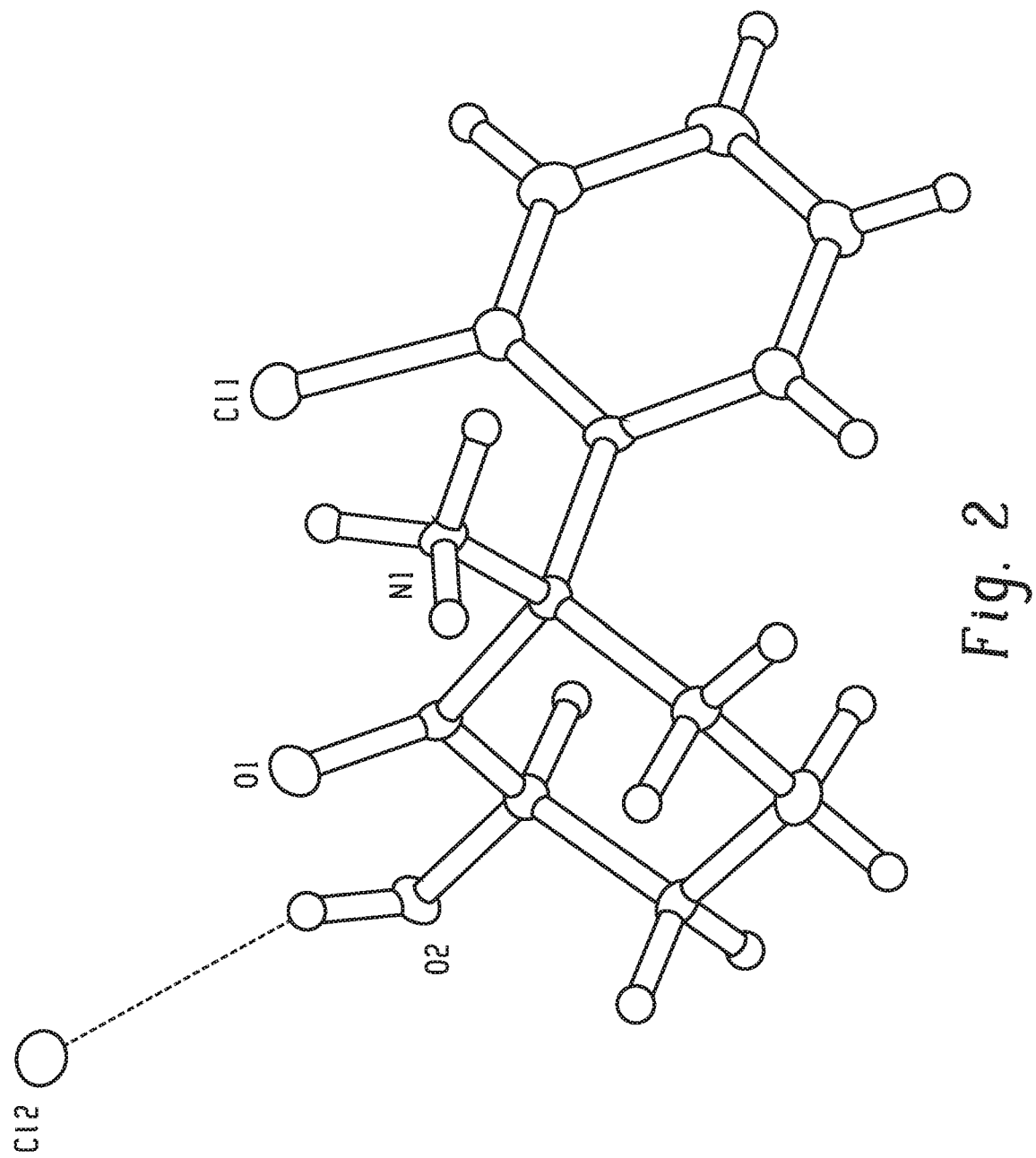
FIG. 2 is a single crystal x-ray structure of (2R,6R)-hydroxynorketamine hydrochloride.

All other hydrogen atoms (H-bonding) were located in the difference map. Their relative positions were restrained using DFIX commands and their thermals freely refined. The absolute stereochemistry of the molecule was established by anomalous dispersion using the Parson's method with a Flack parameter of 0.023(32). A depiction of the crystal structure is shown in FIG. 2. Crystallographic data are summarized in Tables 7-12.

TABLE 7

Crystal data and structure refinement for (2R,6R)-hydroxynorketamine hydrochloride

| Property | Result |
|---|---|
| Temperature | 100.0 K |
| Wavelength | 0.71073 Å |
| Crystal system | Monoclinic |
| Space group | P 1 21 1 |
| Unit cell dimensions | a = 7.3549(6) Å $\alpha$ = 90°. |
| | b = 7.4932(5) Å $\beta$ = 96.868(2)°. |
| | c = 11.3404(12) Å $\gamma$ = 90°. |
| Volume | 621.02(8) Å$^3$ |
| Z | 2 |
| Density (calculated) | 1.477 Mg/m$^3$ |
| Absorption coefficient | 0.511 mm$^{-1}$ |
| F(000) | 288 |
| Crystal size | 0.157 × 0.131 × 0.098 mm$^3$ |
| Crystal color, habit | Colorless Block |
| Theta range for data collection | 1.807 to 28.290° |
| Index ranges | −9 <= h <= 9, −9 <= k <= 9, −14 <= l <= 14 |
| Reflections collected | 7618 |
| Independent reflections | 2927 [R(int) = 0.0350] |
| Completeness to theta = 25.000° | 100.0% |
| Absorption correction | Semi-empirical from equivalents |
| Max. and min. transmission | 0.0962 and 0.0687 |
| Refinement method | Full-matrix least-squares on F$^2$ |
| Data/restraints/parameters | 2927/5/170 |
| Goodness-of-fit on F$^2$ | 1.040 |
| Final R indices [I > 2sigma(I)] | R1 = 0.0265, wR2 = 0.0659 |
| R indices (all data) | R1 = 0.0280, wR2 = 0.0669 |
| Absolute structure parameter | 0.02(3) |
| Extinction coefficient | n/a |
| Largest diff. peak and hole | 0.283 and −0.201 e.Å$^{-3}$ |

TABLE 8

Atomic coordinates (×10$^4$) and equivalent isotropic displacement parameters (Å$^2$ × 10$^3$) for (2R,6R)-hydroxynorketamine hydrochloride. U(eq) is defined as one third of the trace of the orthogonalized U$^{ij}$ tensor.

| | x | y | z | U(eq) |
|---|---|---|---|---|
| Cl(1) | 3437(1) | 8068(1) | 8636(1) | 20(1) |
| O(1) | 4777(2) | 7045(2) | 6149(1) | 18(1) |
| O(2) | 8078(2) | 5975(2) | 7255(2) | 18(1) |
| N(1) | 1437(2) | 5707(3) | 6311(2) | 14(1) |
| C(1) | 4777(3) | 5763(3) | 6802(2) | 13(1) |
| C(2) | 6518(3) | 4905(3) | 7374(2) | 14(1) |
| C(3) | 6698(3) | 3100(4) | 6768(2) | 16(1) |
| C(4) | 5001(3) | 1942(3) | 6824(2) | 17(1) |
| C(5) | 3260(3) | 2934(3) | 6323(2) | 16(1) |
| C(6) | 3023(3) | 4721(3) | 6968(2) | 13(1) |
| C(7) | 2670(3) | 4523(3) | 8268(2) | 14(1) |
| C(8) | 2804(3) | 5944(3) | 9065(2) | 16(1) |
| C(9) | 2415(3) | 5767(4) | 10223(2) | 20(1) |
| C(10) | 1875(3) | 4126(4) | 10622(2) | 23(1) |
| C(11) | 1718(3) | 2687(3) | 9853(2) | 21(1) |
| C(12) | 2095(3) | 2883(4) | 8689(2) | 18(1) |
| Cl(2) | 9623(1) | 9516(1) | 6291(1) | 17(1) |

TABLE 9

Bond lengths [Å] and angles [°] for (2R,6R)-hydroxynorketamine hydrochloride

| Bond | Bond Length (Å) | Bonds in Angle | Bond Angle (°) |
|---|---|---|---|
| Cl(1)—C(8) | 1.743(2) | C(2)—O(2)—H(2) | 114(2) |
| O(1)—C(1) | 1.214(3) | H(1A)—N(1)—H(1B) | 105(3) |
| O(2)—H(2) | 0.90(2) | H(1A)—N(1)—H(1C) | 105(3) |
| O(2)—C(2) | 1.419(3) | H(1B)—N(1)—H(1C) | 109(3) |
| N(1)—H(1A) | 0.92(2) | C(6)—N(1)—H(1A) | 115.0(18) |
| N(1)—H(1B) | 0.94(2) | C(6)—N(1)—H(1B) | 111.9(18) |
| N(1)—H(1C) | 0.95(2) | C(6)—N(1)—H(1C) | 110.2(17) |
| N(1)—C(6) | 1.502(3) | O(1)—C(1)—C(2) | 122.56(19) |

TABLE 9-continued

Bond lengths [Å] and angles [°] for (2R,6R)-hydroxynorketamine hydrochloride

| Bond | Bond Length (Å) | Bonds in Angle | Bond Angle (°) |
|---|---|---|---|
| C(1)—C(2) | 1.508(3) | O(1)—C(1)—C(6) | 122.52(19) |
| C(1)—C(6) | 1.539(3) | C(2)—C(1)—C(6) | 114.35(19) |
| C(2)—H(2A) | 1.0000 | O(2)—C(2)—C(1) | 111.90(18) |
| C(2)—C(3) | 1.530(3) | O(2)—C(2)—H(2A) | 109.2 |
| C(3)—H(3A) | 0.9900 | O(2)—C(2)—C(3) | 109.99(17) |
| C(3)—H(3B) | 0.9900 | C(1)—C(2)—H(2A) | 109.2 |
| C(3)—C(4) | 1.528(3) | C(1)—C(2)—C(3) | 107.32(18) |
| C(4)—H(4A) | 0.9900 | C(3)—C(2)—H(2A) | 109.2 |
| C(4)—H(4B) | 0.9900 | C(2)—C(3)—H(3A) | 109.3 |
| C(4)—C(5) | 1.531(3) | C(2)—C(3)—H(3B) | 109.3 |
| C(5)—H(5A) | 0.9900 | H(3A)—C(3)—H(3B) | 108.0 |
| C(5)—H(5B) | 0.9900 | C(4)—C(3)—C(2) | 111.61(18) |
| C(5)—C(6) | 1.546(3) | C(4)—C(3)—H(3A) | 109.3 |
| C(6)—C(7) | 1.535(3) | C(4)—C(3)—H(3B) | 109.3 |
| C(7)—C(8) | 1.393(3) | C(3)—C(4)—H(4A) | 109.4 |
| C(7)—C(12) | 1.401(3) | C(3)—C(4)—H(4B) | 109.4 |
| C(8)—C(9) | 1.385(3) | C(3)—C(4)—C(5) | 111.11(19) |
| C(9)—H(9) | 0.9500 | H(4A)—C(4)—H(4B) | 108.0 |
| C(9)—C(10) | 1.385(4) | C(5)—C(4)—H(4A) | 109.4 |
| C(10)—H(10) | 0.9500 | C(5)—C(4)—H(4B) | 109.4 |
| C(10)—C(11) | 1.383(4) | C(4)—C(5)—H(5A) | 109.1 |
| C(11)—H(11) | 0.9500 | C(4)—C(5)—H(5B) | 109.1 |
| C(11)—C(12) | 1.390(3) | C(4)—C(5)—C(6) | 112.40(18) |
| C(12)—H(12) | 0.9500 | H(5A)—C(5)—H(5B) | 107.9 |
| | | C(6)—C(5)—H(5A) | 109.1 |
| | | C(6)—C(5)—H(5B) | 109.1 |
| | | N(1)—C(6)—C(1) | 107.57(18) |
| | | N(1)—C(6)—C(5) | 108.39(17) |
| | | N(1)—C(6)—C(7) | 108.37(17) |
| | | C(1)—C(6)—C(5) | 103.73(16) |
| | | C(7)—C(6)—C(1) | 114.02(17) |
| | | C(7)—C(6)—C(5) | 114.42(19) |
| | | C(8)—C(7)—C(6) | 122.9(2) |
| | | C(8)—C(7)—C(12) | 116.8(2) |
| | | C(12)—C(7)—C(6) | 120.3(2) |
| | | C(7)—C(8)—Cl(1) | 121.18(17) |
| | | C(9)—C(8)—Cl(1) | 116.4(2) |
| | | C(9)—C(8)—C(7) | 122.4(2) |
| | | C(8)—C(9)—H(9) | 120.1 |
| | | C(8)—C(9)—C(10) | 119.7(2) |
| | | C(10)—C(9)—H(9) | 120.1 |
| | | C(9)—C(10)—H(10) | 120.3 |
| | | C(11)—C(10)—C(9) | 119.4(2) |
| | | C(11)—C(10)—H(10) | 120.3 |
| | | C(10)—C(11)—H(11) | 119.8 |
| | | C(10)—C(11)—C(12) | 120.4(2) |
| | | C(12)—C(11)—H(11) | 119.8 |
| | | C(7)—C(12)—H(12) | 119.4 |
| | | C(11)—C(12)—C(7) | 121.3(2) |
| | | C(11)—C(12)—H(12) | 119.4 |

TABLE 10

Anisotropic displacement parameters (Å$^2$ × 10$^3$) for(2R,6R)-hydroxynorketamine hydrochloride. The anisotropic displacement factor exponent takes the form: $-2\pi^2[h^2 a^{*2}U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| Cl(1) | 26(1) | 15(1) | 20(1) | −3(1) | 3(1) | −2(1) |
| O(1) | 18(1) | 17(1) | 19(1) | 4(1) | 5(1) | 0(1) |
| O(2) | 12(1) | 19(1) | 22(1) | 3(1) | 2(1) | −1(1) |
| N(1) | 13(1) | 16(1) | 14(1) | −1(1) | 2(1) | 1(1) |
| C(1) | 13(1) | 14(1) | 13(1) | −3(1) | 4(1) | 0(1) |
| C(2) | 13(1) | 15(1) | 16(1) | 1(1) | 2(1) | −1(1) |
| C(3) | 15(1) | 15(1) | 19(1) | −1(1) | 2(1) | 5(1) |
| C(4) | 18(1) | 15(1) | 21(1) | −2(1) | 1(1) | 1(1) |
| C(5) | 16(1) | 16(1) | 16(1) | −3(1) | 1(1) | 0(1) |
| C(6) | 11(1) | 14(1) | 14(1) | 0(1) | 1(1) | 1(1) |
| C(7) | 12(1) | 18(1) | 14(1) | 2(1) | 1(1) | 1(1) |
| C(8) | 14(1) | 18(1) | 18(1) | 2(1) | 1(1) | 1(1) |
| C(9) | 18(1) | 26(1) | 16(1) | −2(1) | 1(1) | 4(1) |
| C(10) | 18(1) | 34(2) | 16(1) | 6(1) | 4(1) | 3(1) |
| C(11) | 17(1) | 24(1) | 23(1) | 8(1) | 2(1) | 0(1) |
| C(12) | 15(1) | 20(1) | 19(1) | 1(1) | 2(1) | −2(1) |
| Cl(2) | 19(1) | 15(1) | 16(1) | 1(1) | 1(1) | 1(1) |

TABLE 11

Hydrogen coordinates (×10$^4$) and isotropic displacement parameters (Å$^2$ × 10$^3$) for (2R,6R)-hydroxynorketamine hydrochloride.

| | x | y | z | U(eq) |
|---|---|---|---|---|
| H(2) | 7830(50) | 7000(40) | 6860(30) | 41(10) |
| H(1A) | 1540(40) | 6930(30) | 6330(20) | 22(8) |
| H(1B) | 1270(40) | 5410(40) | 5500(20) | 23(7) |
| H(1C) | 340(30) | 5450(40) | 6650(20) | 20(7) |
| H(2A) | 6423 | 4708 | 8236 | 17 |
| H(3A) | 6881 | 3297 | 5928 | 20 |
| H(3B) | 7788 | 2467 | 7160 | 20 |
| H(4A) | 4913 | 1604 | 7659 | 21 |
| H(4B) | 5117 | 834 | 6364 | 21 |
| H(5A) | 2184 | 2166 | 6396 | 19 |
| H(5B) | 3304 | 3172 | 5468 | 19 |
| H(9) | 2518 | 6766 | 10741 | 24 |
| H(10) | 1614 | 3989 | 11417 | 27 |
| H(11) | 1351 | 1557 | 10123 | 26 |
| H(12) | 1960 | 1887 | 8168 | 21 |

TABLE 12

Hydrogen bonds for (2R,6R)-hydroxynorketamine hydrochloride [Å and °].

| D-H . . . A | d(D-H) | d(H . . . A) | d(D . . . A) | <(DHA) |
|---|---|---|---|---|
| O(2)—H(2) . . . Cl(2) | 0.90(2) | 2.43(3) | 3.1348(18) | 135(3) |
| N(1)—H(1A) . . . Cl(2)#1 | 0.92(2) | 2.39(3) | 3.149(2) | 140(2) |
| N(1)—H(1B) . . . Cl(2)#2 | 0.94(2) | 2.16(2) | 3.095(2) | 169(2) |
| N(1)—H(1C) . . . O(2)#1 | 0.95(2) | 1.92(2) | 2.816(2) | 156(3) |

Symmetry transformations used to generate equivalent atoms:
1 x + 1, y, z
2 −x + 1, y + ½, −z + 1

Example 12. PXRD of (2R,6R)-Hydroxynorketamine Hydrochloride

Figure 3:
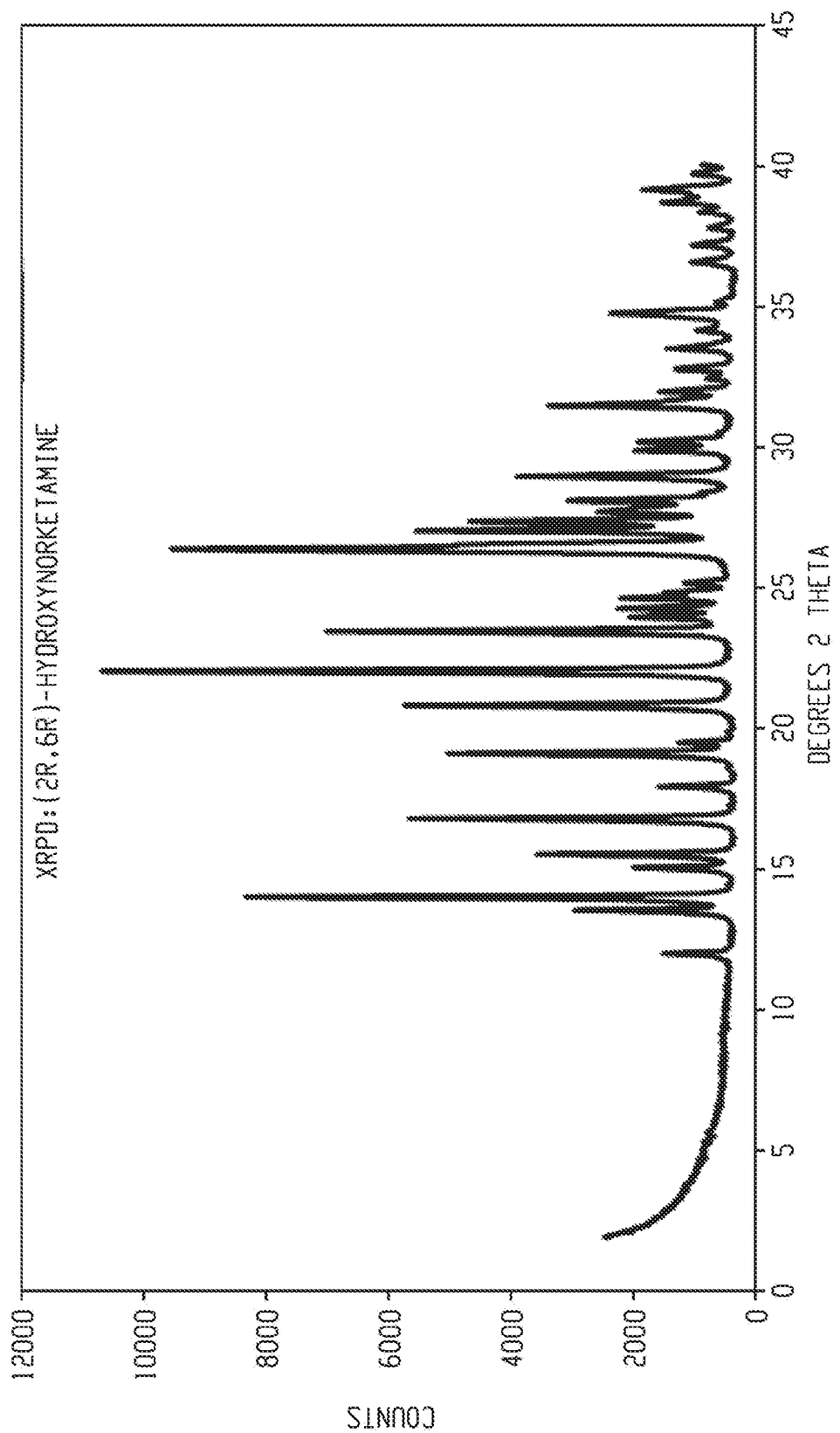
FIG. 3 is an XPRD spectra of ((2R,6R)-hydroxynorketamine hydrochloride.

A powder x-ray diffraction spectra of (2R,6R)-hydroxynorketamine hydrochloride is shown in FIG. 3. 5-10 mg of (2R,6R)-hydroxynorketamine hydrochloride was added to a PXRD sample holder.

The Rigaku Smart-Lab X-ray diffraction system was configured for reflection Bragg-Brentano geometry using a line source X-ray beam. The x-ray source is a Cu Long FineFocus tube that was operated at 40 kV and 44 ma. That source provides an incident beam profile at the sample that changes from a narrow line at high angles to a broad rectangle at low angles. Beam conditioning slits are used on the line X-ray source toe nsure that the maximum beam size is less than 10 mm both along the line and normal to the line.

The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1°2θ or less. The axial divergence of the X-ray beam is controlled by 5.0-degree Soller slits in both the incident and diffracted beam paths. Powder samples were prepared in a low background Si holder using light manual pressure to keep the sample surfaces flat and level with the reference surface of the sample holder.

The powder was pressed down gently with the sample flattening tool and the sample holder was placed in the sample changer. Each sample was analyzed from 2 to 40°2θ using a continuous scan of 6°2θ per minute with an effective step size of 0.02°2θ.

Run Parameters: Soller (inc.) 5.0 deg, IHS 10.0 mm, SS 1.250 deg, DS 1.250 deg, Soller (rec) 5.0 deg, RS 0.3 mm, Scan Axis Theta/2-Theta, Mode Continuous, Start (deg) 3.0, Stop (deg) 45.0, Step (deg) 0.020, Speed (deg/min) 2.5, Spin-yes, Voltage (kV) 40, Current (mA) 15. The spectra demonstrates the following characteristic peaks (2θ).

TABLE 13

| No. | 2 θ |
|---|---|
| 1 | 12.1 |
| 2 | 13.6 |
| 3 | 14.1 |
| 4 | 15.1 |
| 5 | 15.6 |
| 6 | 16.9 |
| 7 | 18.0 |
| 8 | 19.2 |
| 9 | 19.5 |
| 10 | 20.8 |
| 11 | 22.1 |
| 12 | 23.5 |
| 13 | 24.0 |
| 14 | 24.3 |
| 15 | 24.6 |
| 16 | 24.8 |
| 17 | 25.2 |
| 18 | 26.4 |
| 19 | 27.0 |
| 20 | 27.4 |
| 21 | 27.7 |
| 22 | 28.1 |
| 23 | 28.9 |
| 24 | 29.9 |
| 25 | 30.2 |
| 26 | 31.5 |
| 27 | 31.9 |
| 28 | 32.4 |
| 29 | 32.7 |
| 30 | 33.5 |
| 31 | 34.1 |
| 32 | 34.7 |
| 33 | 36.5 |
| 34 | 37.1 |
| 35 | 37.7 |
| 36 | 38.3 |
| 37 | 38.7 |
| 38 | 39.1 |
| 39 | 39.6 |

Example 13. TGA and DSC of (2R, 6R)-Hydroxynorketamine Hydrochloride

Figure 4:
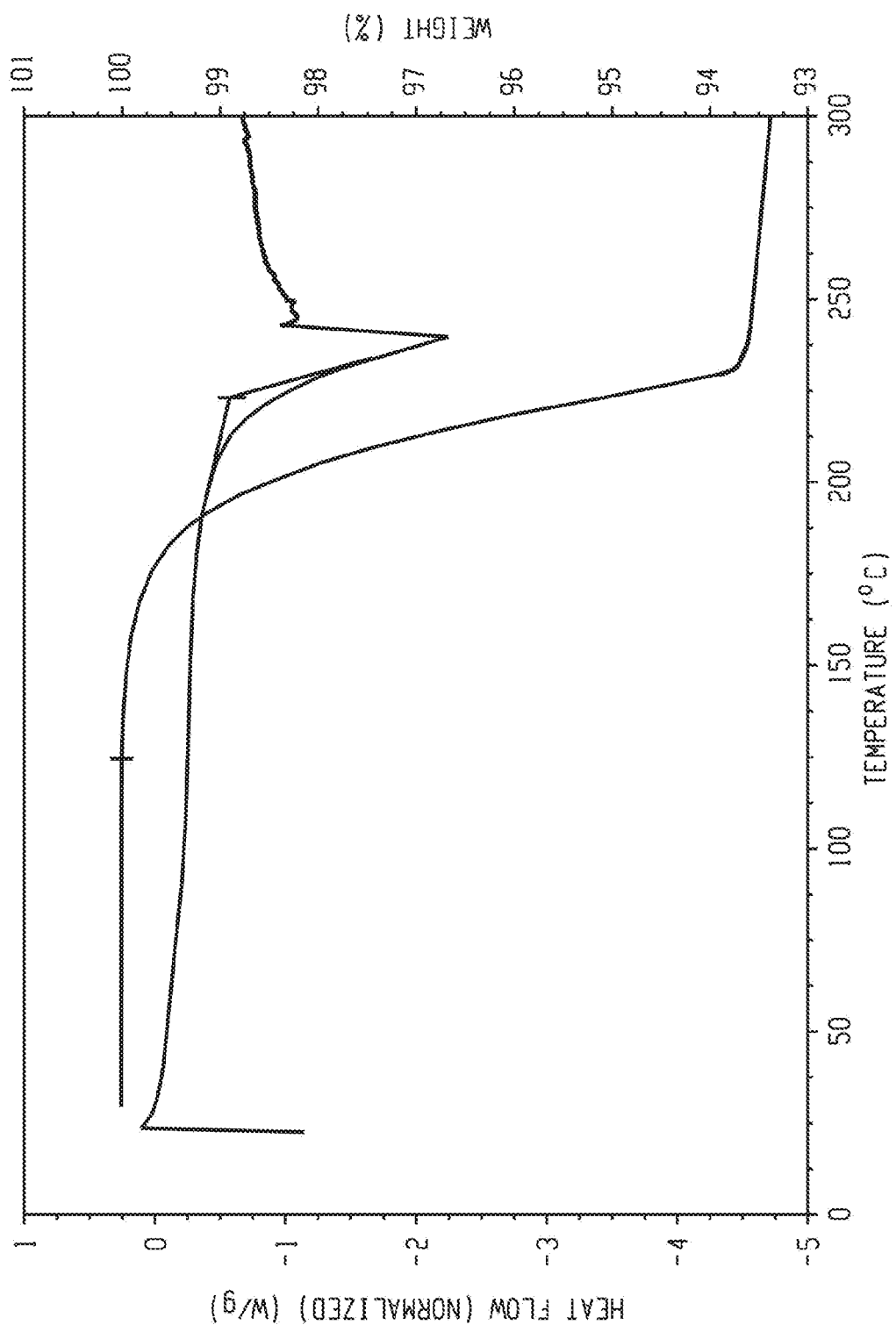
FIG. 4 is a DSC and TGA of ((2R,6R)-hydroxynorketamine hydrochloride. The DSC profile exhibits an endotherm with an onset at 223.0° C. and a min. The TGA trace exhibits a weight loss of approximately 0.02% from 20° C. to 120° C.

Thermogravimetric analysis and differential scanning calorimetry plots for (2R,6R)-hydroxynorketamine hydrochloride are shown in FIG. 4. For the DSC 1-3 mg of (2R,6R)-HNK was weighed into a TZero pan. A TZero lid was placed on the pan and gently pressed down. The pan was then transferred to the DSC for analysis at 10° C./min up to 300° C. A DSC standard was made by the same procedure but without HNK. For TGA standard aluminum pan was placed into the platinum TGA pan and the blank was tared with the instrument. 1-5 mg of (2R,6R)-HNK was added to the standard aluminum pan and analyzed at 10° C./min up to 300° C. The sample exhibited a weight loss of 0.02% out to ~125° C. This weight loss is likely due to residual solvent and suggests the material is anhydrous. An onset of melt was observed at 223.017° C.

Example 14. Synthesis of 2-Chlorophenyl Cyclopentylketone

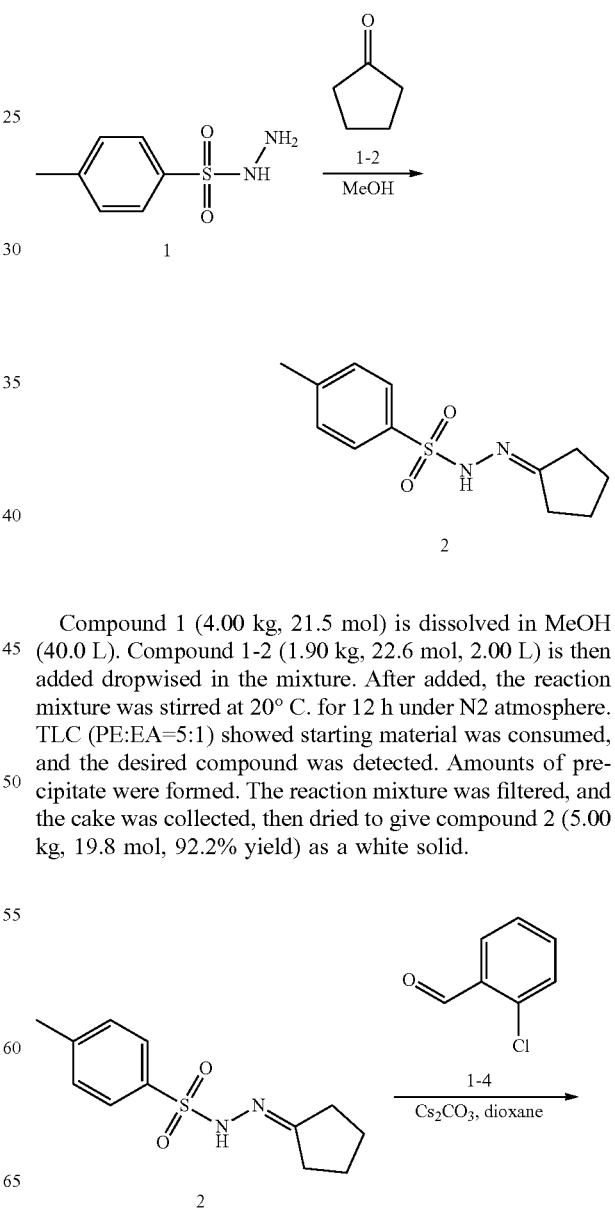

Compound 1 (4.00 kg, 21.5 mol) is dissolved in MeOH (40.0 L). Compound 1-2 (1.90 kg, 22.6 mol, 2.00 L) is then added dropwised in the mixture. After added, the reaction mixture was stirred at 20° C. for 12 h under N2 atmosphere. TLC (PE:EA=5:1) showed starting material was consumed, and the desired compound was detected. Amounts of precipitate were formed. The reaction mixture was filtered, and the cake was collected, then dried to give compound 2 (5.00 kg, 19.8 mol, 92.2% yield) as a white solid.

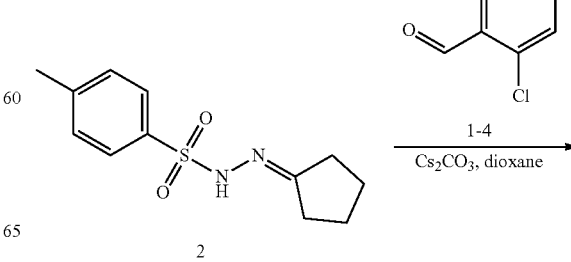

-continued

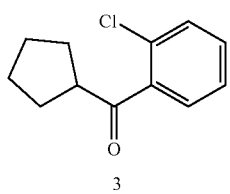

A solution of compound 1-4 (1.51 kg, 10.8 mol, 1.34 L), compound 2 (3 kg, 11.9 mol) and Cs₂CO₃ (5.28 kg, 16.2 mol) in 1,4-dioxane (40.0 L) was stirred at 100-110° C. for 48 hours. TLC (PE:EA=5:1) showed starting material was consumed, and the desired compound was detected. The reaction mixture was filtered and concentrated in vacuum to give a residue. The residue was triturated with PE (20 L) to give compound 3 (2.00 kg, crude) as a red oil.

Example 15. Preparation of Norketamine

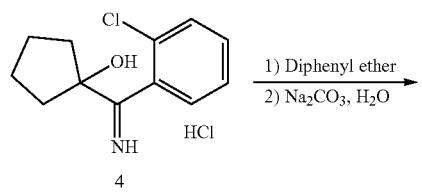

Compound 4 (300 g, 1.15 mmol, HCl) was dissolved in diphenyl oxide (3.00 L), the mixture was stirred at 170-185° C. for 15 min. TLC (PE:EA=1:1, starting material: R$_f$=0.6, product: R$_f$=0.5) showed starting material was consumed, and one new pot was detected. The reaction mixture was cooled to 25-30° C., added water (6 L), then filtered. The filtrate was extracted with EtOAc (2 L*3). The aqueous layer was adjusted pH=8-9 with sat Na₂CO₃ solution, then extracted with EtOAc (2 L*2), the combined organic layers were washed with brine (1 L), dried over Na₂SO₄, filtered, and the filtrate was concentrated under reduced pressure to give compound 13 (1.10 kg, 61.0% yield) as a yellow solid.

Example 16. Preparation of tert-butyl ((1R,3R)-1-(2-chlorophenyl)-3-hydroxy-2-oxocyclohexyl)carbamate

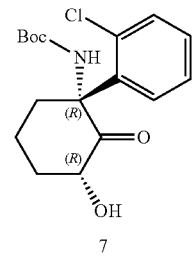

Compound 6 (200 g, 485 mmol) was dissolved in THF (4.00 L) and H₂O (200 mL), and then added to Formic Acid (200 mL, 98% purity), the mixture was stirred at 15° C. for 1 h. HPLC showed starting material was consumed, and the desired compound was detected. The reaction mixture was quenched by addition sat.Na₂CO₃ (2 L) and sat.NaHCO₃ (2 L), and then extracted with EtOAc (2 L*3). The combined organic layers were washed with brine (1 L), dried over Na₂SO₄, filtered and concentrated under reduced pressure to give a residue. The residue was purified by column chromatography (SiO₂, Petroleum ether: Ethyl acetate=20:1 to 8:1) to give a yellow gum. And then the gum was triturated with PE (500 mL) to give compound 7 (60 g, 169 mmol, 34.8% yield) as a white solid.

Example 17. Deprotection in Ethyl Acetate to Provide 2R,6R-Hydroxynorketamine Hydrochloride

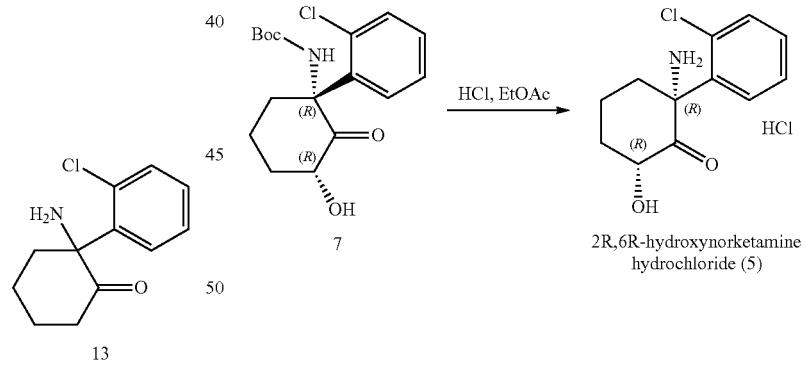

Compound 7 (150 g, 441 mmol) was dissolved in EtOAc (2.00 L). HCl/EtOAc (4 M, 331 mL) was then added to the mixture at 15° C. under Na. After addition, the reaction mixture was stirred at 15° C. for 12 h. A precipitate was formed. TLC (PE:EA=2:1) showed the starting material was consumed, and the desired compound was detected. The mixture was filtered, washed with EtOAc (1 L), PE (1 L) in return and dried under vacuum to give a white solid. The white solid was combined with other batches, then triturated with EtOAc (3.5 L) and MeOH (100 mL) to give compound 5, 2R,6R-hydroxynorketamine hydrochloride as a white solid.

Example 18. Preparation of (1S,3R)-3-((tert-butoxycarbonyl)amino)-3-(2-chlorophenyl)-2-oxocyclohexyl 4-nitrobenzoate (10a)

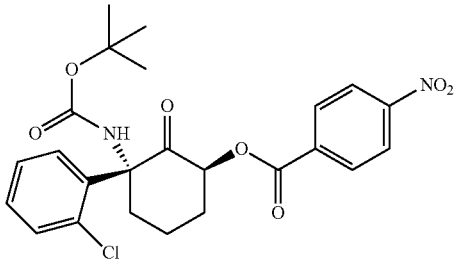

(10A)

tert-Butyl ((1R,3R)-1-(2-chlorophenyl)-3-hydroxy-2-oxocyclohexyl)carbamate (8A) (2.82 grams, 8.30 mmol) was placed in a round bottom flask with a stirbar. Dichloromethane (20 ml) was added, followed by pyridine (1.31 grams, 16.6 mmol). The reaction was stirred until all reagents dissolved, then placed under a nitrogen atmosphere and cooled to 0° C. Then trifluoromethanesulfonic anhydride (1.0 M in dichloromethane, 9.43 mL, 9.43 mmol) was added via syringe. The reaction was stirred for 45 minutes at 0° C., then quenched by being poured into a solution of saturated aqueous sodium bicarbonate. The mixture was extracted with dichloromethane, and the solvent removed by rotary evaporation to give the crude triflate (9A), which was used without further purification. The triflate was unstable, and required either immediate use or storage at −80° C.

The crude triflate (3.92 grams, 8.3 mmol, based on 100% yield) was then dissolved in dimethylformamide (50 ml). Then 4-nitrobenzoic acid (5.55 grams, 33.2 mmol, followed by potassium carbonate (1.15 grams, 8.30 mmol) was added. The suspension was stirred vigorously at room temperature for 16 hours. The reaction was then poured into a separatory funnel containing diethyl ether (200 ml) and water (100 me. The organic phase was washed twice with water (100 ml) and once with saturated aqueous sodium chloride (100 ml). The organic phase was taken, and the solvent removed by rotary evaporation. Purification by silica gel chromatography (0% to 100% ethyl acetate in diethyl ether) provided the title compound.

$^1$H NMR (400 MHz, Chloroform-d) δ 8.23-8.11 (m, 2H), 7.95-7.85 (m, 2H), 7.58 (d, J=7.9 Hz, 1H), 7.36-7.27 (m, 1H), 7.27-7.20 (m, 1H), 7.20-7.14 (m, 1H), 5.99 (s, 1H), 5.93 (dd, J=8.7, 4.9 Hz, 1H), 3.19-3.09 (m, 1H), 2.43-2.31 (m, 2H), 2.27-2.00 (m, 3H), 1.32 (s, 9H). $^{13}$C NMR (101 MHz, CDCl$_3$) δ 199.5, 163.3, 153.9, 150.5, 136.2, 134.8, 133.6, 131.3, 130.9, 129.7, 128.6, 126.4, 123.3, 80.5, 76.2, 68.5, 37.9, 33.8, 28.0, 18.9. HRMS (ESI+): Expected 511.1242 [M+Na$^+$] (C$_{24}$H$_{25}$ClN$_2$NaO$_7^+$). Observed 511.1248. [α]$_D^{20}$: +9.5° (c 1.0, chloroform).

Example 19. Preparation of tert-butyl ((1R,3S)-1-(2-chlorophenyl)-3-hydroxy-2-oxocyclohexyl)carbamate (11a)

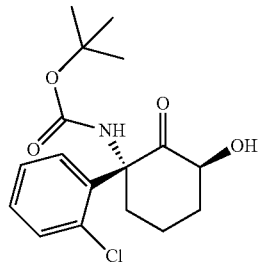

(11A)

(1S,3R)-3-((tert-butoxycarbonyl)amino)-3-(2-chlorophenyl)-2-oxocyclohexyl 4-nitrobenzoate (10A) (2.00 grams, 4.09 mmol) was dissolved in methanol (50 ml). The reaction was cooled to 0° C., and potassium carbonate (0.565 mg, 4.09 mmol) was added. The reaction was stirred for 30 minutes at 0° C. The reaction was then quenched by being poured into an aqueous solution of saturated sodium bicarbonate. The mixture was extracted with ethyl acetate, the organic layer was taken, and the solvent removed by rotary evaporation. Purification by silica gel chromatography (0% to 100% ethyl acetate in hexanes) gave the desired product (11A) in 65% yield.

$^1$H NMR (400 MHz, Chloroform-d) δ 7.45-7.40 (m, 1H), 7.40-7.33 (m, 1H), 7.33-7.23 (m, 2H), 5.28 (s, 1H), 4.65 (dd, J=12.1, 6.5 Hz, 1H), 3.02-2.88 (m, 1H), 2.50-2.40 (m, 1H), 2.19-2.00 (m, 2H), 1.85-1.75 (m, 1H), 1.75-1.64 (m, 1H), 1.38 (s, 1H) $^{13}$C NMR (101 MHz, cdcl$_3$) δ 203.4, 154.3, 136.6, 133.4, 131.8, 129.1, 127.7, 126.7, 81.2, 72.7, 67.8, 38.3, 36.7, 28.1, 19.1 HRMS (ESI+): Expected 362.1130 [M+Na+] (C$_{37}$H$_{22}$ClNaNO$_4^+$). Observed 362.1139. [α]$_D^{20}$: −2.3° (c 1.0, chloroform).

Example 20. Preparation of (2R,6S)-2-amino-2-(2-chlorophenyl)-6-hydroxycyclohexan-1-one (12a)

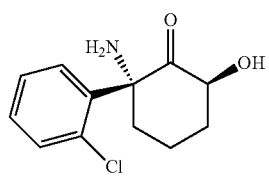

(12A)

tert-butyl ((1R,3S)-1-(2-chlorophenyl)-3-hydroxy-2-oxocyclohexyl)carbamate (11A) (860 mg, 2.5 mmol) was dissolved in dichloromethane (8.0 nil) and cooled to 0° C. Then trifluoroacetic acid (4.0 ml, 52 mmol) was added. The reaction was stirred at 0° C. for 45 minutes. The solvent and trifluoroacetic acid were then removed by rotary evaporation. Ethyl acetate and a pH 7 saturated potassium phosphate buffer was added to the crude material, and the material was transferred to a separatory funnel, where it was extracted with ethyl acetate twice, while keeping the pH between 6 and 7. The organic phase was taken and the solvent removed by rotary evaporation to give a crude white solid. This solid was purified by reverse phase high pressure liquid chromatography (MeCN—H$_2$O mobile phase with 0.1% TFA). The desired fractions were neutralized with pH 7 buffer, extracted with ethyl acetate twice, and the organic phase was taken and the solvent removed by rotary evaporation to give a white solid. The solid was dissolved in ethanol and the ethanol removed by rotary evaporation to give the desired product. Absolute conformation was proven by single crystal x-ray crystallography.

$^1$H NMR (400 MHz, Chloroform-d) δ 7.64-7.58 (m, 1H), 7.43-7.36 (m, 1H), 7.36-7.23 (m, 2H), 4.89 (dd, J=11.8, 6.5 Hz, 1H), 2.59-2.52 (m, 1H), 2.46-2.42 (m, 1H), 2.22-2.08 (m, 1H), 1.98 (ddt, J=14.1, 3.9, 2.5 Hz, 1H), 1.93-1.80 (m, 2H). $^{13}$C NMR (101 MHz, CDCl$_3$) δ 210.3, 141.0, 133.0, 131.1, 129.1, 127.1 (2C), 72.3, 64.9, 39.4, 35.3, 19.4. HRMS (ESI+): Expected 240.0786 [M+H$^+$] (C$_{12}$H$_{15}$ClNO$_2^+$). Observed 240.0794. [α]$_D^{20}$: +75.4° (c 1.0, chloroform)

Example 21. Preparation of (1R,3S)-3-((tert-butoxycarbonyl)amino)-3-(2-chlorophenyl)-2-oxocyclohexyl 4-nitrobenzoate (10)

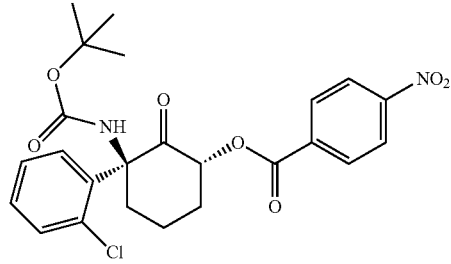 [SMILES: CC(C)(C)OC(=O)N[C@]1(c2ccccc2Cl)CCC[C@@H](OC(=O)c2ccc([N+](=O)[O-])cc2)C1=O]

Compound 10 was synthesized using the tert-Butyl ((1S, 3S)-1-(2-chlorophenyl)-3-hydroxy-2-oxocyclohexyl)carbamate, compound 8 as a starting material.

$^1$H NMR (400 MHz, Chloroform-d) δ 8.27-8.10 (m, 2H), 7.92 (s, 2H), 7.58 (d, J=7.9 Hz, 1H), 7.32 (td, J=7.6, 1.6 Hz, 1H), 7.27-7.12 (m, 2H), 6.03 (s, 1H), 5.94 (dd, J=8.8, 4.9 Hz, 1H), 3.23-2.99 (m, 1H), 2.37 (dq, J=12.5, 6.2 Hz, 2H), 2.28-1.92 (m, 3H), 1.33 (s, 9H). $^{13}$C NMR (101 MHz, cdcl$_3$) δ 200.2, 163.4, 154.0, 150.7, 136.2, 134.8, 133.8, 131.4, 131.0, 129.2, 128.9, 126.5, 123.4, 80.8, 76.5, 68.6, 38.1, 34.2, 28.2, 18.9. [α]$_D^{7°}$: −11° (c 1.0, chloroform).

Example 22. Preparation of tert-butyl ((1S,3R)-1-(2-chlorophenyl)-3-hydroxy-2-oxocyclohexyl)carbamate (11)

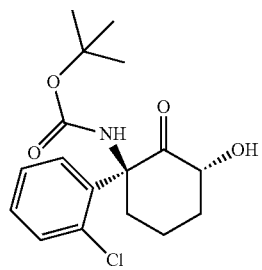

Compound was synthesized in an analogous fashion to its enantiomer (11A), using (1R,3S)-3-((tert-butoxycarbonyl)amino)-3-(2-chlorophenyl)-2-oxocyclohexyl 4-nitrobenzoate as a starting material.

$^1$H NMR (400 MHz, Chloroform-d) δ 7.59-7.21 (m, 4H), 5.15 (s, 1H), 4.71-4.55 (m, 1H), 3.63 (d, J=4.6 Hz, 1H), 3.04-2.90 (m, 1H), 2.47 (ddq, J=12.9, 6.4, 3.2 Hz, 1H), 2.23-2.00 (m, 2H), 1.95-1.68 (m, 2H), 1.39 (s, 9H). $^{13}$C NMR (101 MHz, cdcl$_3$) δ 203.5, 154.4, 136.7, 133.6, 132.0, 129.3, 127.9, 126.9, 72.9, 68.0, 38.5, 36.9, 28.3, 19.3, HRMS (ESI+): Expected 362.1130 [M+Na$^+$] (C$_{17}$H$_{22}$ClNNaO$_4^+$). Observed 362.1135. [α]D$^{20}$: +1.2° (c 1.0, chloroform).

Example 23. Preparation of (2S,6R)-2-amino-2-(2-chlorophenyl)-6-hydroxycyclohexan-1-one (12)

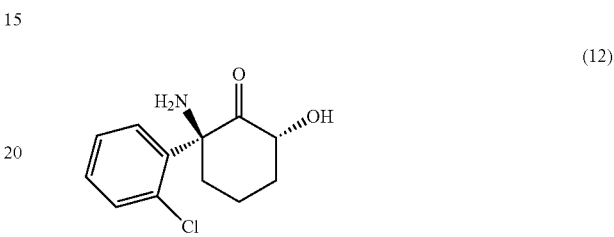

Compound 12 was synthesized in an analogous fashion to its enantiomer (12A), using tert-butyl ((1S,3R)-1-(2-chlorophenyl)-3-hydroxy-2-oxocyclohexyl)carbamate as a starting material.

$^1$H NMR (400 MHz, Chloroform-d): 7.61 (dd, J=1.9, 7.8 Hz, 1H), 7.38 (dd, J=1.5, 7.7 Hz, 1H), 7.30 (dt, J=1.5, 7.7 Hz, 1H), 7.24 (dt, J=1.9, 7.7 Hz, 1H), 4.89 (dd, J=7.0, 12 Hz, 1H), 3.52 (bs, 1H), 2.51 (dt, J=4.4 Hz, 13.6 Hz, 1H), 2.48-2.40 (m, 1H), 2.22-2.07 (m, 1H), 1.99-1.82 (m, 1H), 1.91-1.78 (m, 4H). $^{13}$C NMR (101 MHz, cdcl$_3$) δ 210.3, 141.3, 132.9, 130.9, 128.8, 126.9 (2C), 72.0, 64.6, 39.4, 35.2, 19.4. HRMS (ESI+): Expected 240.0786 [M+H$^+$] (C$_{12}$H$_{14}$ClNNaO$_2^+$). Observed 240.0786. Rotation: −73.6° (c 1.0, chloroform).

Example 24. Recrystallization of 2R,6R-Hydroxynorketamine 100.25 grams 2R,6R-hydroxynorketamine hydrochloride was dissolved in 100 mL of water.

Acetone (2000 ml) was added at rate of 0.75 equivalents (75 ml) per minute. Nucleation noted at 5 minutes, 20 seconds. The reaction was stirred for 2 hours, then filtered and vacuum dried overnight to give the final product in good yield.

SPECIFIC EMBODIMENTS

Embodiment 1. A crystalline form of (2R,6R)-hydroxynorketamine hydrochloride characterized by single crystal parameters approximately equal to the following:
cell dimensions comprising
a=7.35 Å alpha=90°
b=7.49 Å beta=96.87°
c=11.35 Å gamma=90°
V=621.02 Å$^3$; and
space group=P 1 21 1, crystal system=monoclinic, molecules per unit cell=1, density (calculated)=1.477 mg/m$^3$.

Embodiment 2. The crystalline form of embodiment 1, wherein the crystalline form contains no detectable amounts of other hydroxynorketamine or hydroxynorketamine salts crystalline forms as determined by x-ray powder diffraction.

Embodiment 3. A crystalline form of (2S,6S)-hydroxynorketamine hydrochloride characterized by single crystal parameters approximately equal to the following:

cell dimensions comprising a=7.35 Å alpha=90° b=7.48 Å beta=96.87° c=11.34 Å gamma=90°

V=619.32 Å$^3$; and space group=P 1 21 1, crystal system=monoclinic, molecules per unit cell=1, density (calculated)=1.481 Mg/m$^3$.

Embodiment 4. The crystalline form of embodiment 3, wherein the crystalline form contains no detectable amounts of other hydroxynorketamine or hydroxynorketamine salts crystalline forms as determined by x-ray powder diffraction.

Embodiment 5. A method for the chiral resolution of norketamine, comprising adding (D)-(R)-pyroglutamic acid to racemic norketamine in a solvent, forming solid (S)-norketamine D-pyroglutamate.

Embodiment 6. The method of embodiment 5, additionally comprising converting the (S)-norketamine D-pyroglutamate to (S)-norketamine.

Embodiment 7. A method for the chiral resolution of norketamine, comprising adding (L)-(S)-pyroglutamic acid to racemic norketamine in a solvent, forming solid (R)-norketamine L-pyroglutamate, and converting (R)-norketamine L-pyroglutamate to (R)-norketamine.

Embodiment 8. A method for the manufacture of (2R,6R)-hydroxynorketamine or (2S,6S)-hydroxynorketamine, or a salt thereof, the method comprising

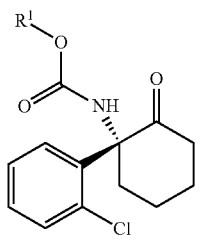

Formula Ia

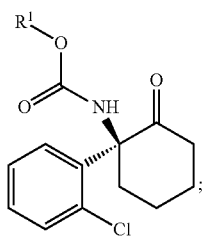

Formula Ib treating a compound of Formula Ia or Formula Ib with a base, then with a trialkylsilylchloride, then with a peroxy compound, and then optionally with an acid or a fluoride source, to provide a compound of Formula IIa if Formula Ia was treated or a compound of Formula IIb if Formula Ib was treated, wherein the compound of Formula IIa or Formula IIb contains a carbamate linkage;

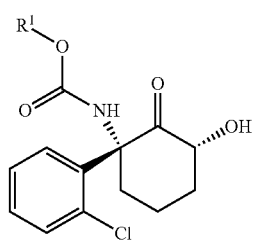

Formula IIa

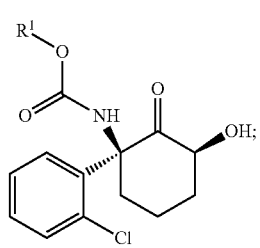

Formula IIb and
cleaving the carbamate linkage in the compound of Formula IIa or Formula IIb to provide (2R,6R)-hydroxynorketamine if the carbamate linkage of the compound of Formula IIa was cleaved, or (2S,6S)-hydroxynorketamine if the carbamate linkage of the compound of Formula IIb was cleaved

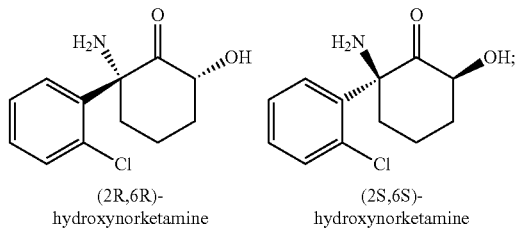

(2R,6R)-hydroxynorketamine   (2S,6S)-hydroxynorketamine wherein R$^1$ is C$_1$-C$_6$ alkyl, C$_1$-C$_6$ haloalkyl, benzyl, 4-methoxybenzyl, or 2-trimethylsilylethyl.

Embodiment 9. The method according to embodiment 8, wherein R$^1$ is tert-butyl and wherein cleaving the carbamate linkage comprises treatment of the compound of Formula IIa or Formula IIb with acid.

Embodiment 10. The method according to embodiment 9, wherein the acid is trifluoroacetic acid.

Embodiment 11. The method according to embodiment 8, additionally comprising treating (2R,6R)-hydroxynorketamine with hydrochloric acid to manufacture (2R,6R)-hydroxynorketamine hydrochloride salt, or treating (2S,6S)-hydroxynorketamine with hydrochloric acid to manufacture (2S,6S)-hydroxynorketamine hydrochloride salt.

Embodiment 12. The method according to embodiment 8 wherein the base used for treating the compound of Formula Ia or Formula Ib with is a strong base.

Embodiment 13. The method according to embodiment 12, wherein the strong base is lithium diisopropylamide, sodium hexamethyldisilazane, potassium hexamethyldisilazane, or sec-butyllithium, and the compound of Formula Ia or Formula Ib is treated with the strong base at a temperature below 0° C.

Embodiment 14. The method according to embodiment 8 wherein treating the compound of Formula Ia or Formula Ib with a base comprises treating the compound of Formula Ia or Formula Ib with lithium diisopropylamide at a temperature below −50° C.

Embodiment 15. The method according to any one of embodiments 8-14 wherein the trialkylsilylchloride is trimethylsilyl chloride, triethylsilyl chloride, tert-butyldimethylsilyl chloride, or triisopropylsilyl chloride.

Embodiment 16. The method according to embodiment 15 wherein the trialkylsilylchloride is trimethylsilyl chloride Embodiment 17. The method according to any one of embodiments 8-16, wherein the peroxy compound is a peroxy acid or a peroxide.

Embodiment 18. The method according to embodiment 17, wherein the peroxy compound is meta-chloroperoxybenzoic acid, peroxybenzoic acid, peracetic acid, dimethyldioxirane, tert-butylhydroperoxide, or hydrogen peroxide.

Embodiment 19. The method according to any one of embodiments 8-18, wherein after treatment with the peroxy compound the compound of Formula Ia or Formula Ib is treated with tetra-n-butylammonium fluoride.

Embodiment 20. The method according to any one of embodiments 8-19 wherein the peroxy compound is meta-chloroperoxybenzoic acid.

Embodiment 21. The method according to any one of embodiments 8-20, further comprising generating the compound of Formula Ia or Formula Ib by reacting (R)-norketamine with $(R^1O_2C)_2O$ or $R^1O_2C$—X to generate a compound of Formula Ia, or reacting (S)-norketamine with $(R^1O_2C)_2O$ or $R^1O_2C$—X to generate a compound of Formula Ib; wherein X is a halogen.

Embodiment 22. The method according to embodiment 21 wherein $R^1$ is tert-butyl, and wherein generating the compound of Formula Ia comprises reacting (R)-norketamine with (tert-butyl-$O_2C$)$_2$O, and generating the compound of Formula Ib comprises reacting (S)-norketamine with (tert-butyl-$O_2C$)$_2$O.

Embodiment 23. The method according to embodiment 8, comprising

Formula Ia

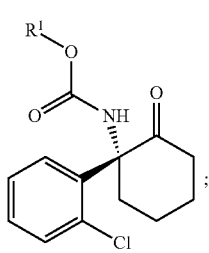

treating a compound of Formula Ia with lithium diisopropylamide at a temperature below −50° C., then with trimethylsilylchloride, then with meta-chloroperoxybenzoic acid, and then with tetra-n-butylammonium fluoride, to provide a compound of Formula IIa, wherein $R^1$ is tert-butyl, Formula IIa

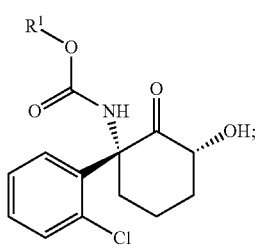

and
cleaving the carbamate linkage in Formula IIa by treatment with acid to provide (2R,6R)-hydroxynorketamine

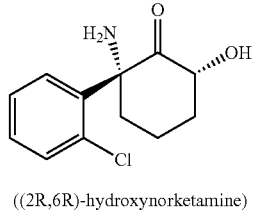 [SMILES: N[C@@]1(c2ccccc2Cl)CCC[C@@H](O)C1=O]

((2R,6R)-hydroxynorketamine)

Embodiment 24. The method according to embodiment, comprising

Formula Ib

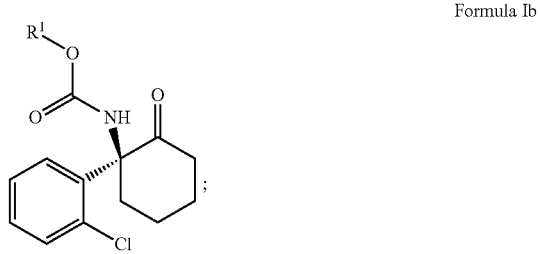

treating the compound of Formula Ib with lithium diisopropylamide at a temperature below −50° C., then with trimethylsilylchloride, then with meta-chloroperoxybenzoic acid, and then with tetra-n-butylammonium fluoride, to provide a compound of Formula IIb, wherein $R^1$ is tert-butyl, Formula IIb

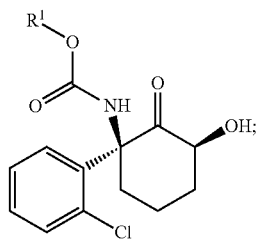

and
cleaving the carbamate linkage in Formula IIb by treatment with acid to provide (2S,6S)-hydroxynorketamine

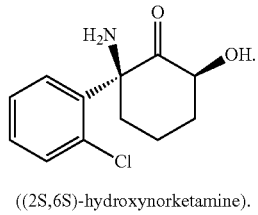 [SMILES: N[C@]1(c2ccccc2Cl)CCC[C@H](O)C1=O]

((2S,6S)-hydroxynorketamine).

Embodiment 25. A crystalline form of (2R,6R)-hydroxynorketamine exhibiting a XRPD spectra at characteristic peaks at any combination of at least 4, of at least 5, at least 8, at least 10, or at least 12, or at least 15 of the following (20) values: 12.1, 13.6, 14.1, 15.1, 15.6, 16.9, 18.0, 19.2, 19.5, 20.8, 22.1, 23.5, 24.0, 24.3, 24.6, 24.8, 25.2, 26.4, 27.0, 27.4, 27.7, 28.1, 29.9, 30.2, 31.5, 31.9, 32.4, 32.7, 33.5, 34.7, 36.5, 37.1, 37.7, 38.3, 38.7, 39.1, and 39.6.

Embodiment 26. A crystalline form of (2R,6R)-hydroxynorketamine exhibiting a XRPD spectra substantially as shown in FIG. 3.

What is claimed is:

1. A method for the manufacture of (2R,6R)-hydroxynorketamine or (2S,6S)-hydroxynorketamine, or a salt thereof, the method comprising

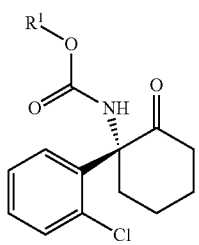

Formula Ia

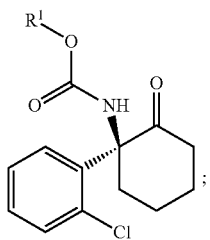

Formula Ib treating a compound of Formula Ia or Formula Ib with a base, then with a trialkylsilylchloride, then with a peroxy compound, and then optionally with an acid or a fluoride source, to provide a compound of Formula II if Formula Ia was treated or a compound of Formula IIb if Formula Ib was treated, wherein the compound of Formula IIa or Formula IIb contains a carbamate linkage;

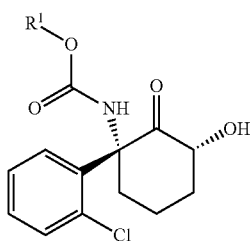

Formula IIa

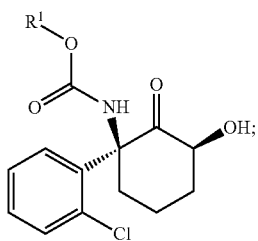

Formula IIb and cleaving the carbamate linkage in the compound of Formula IIa or Formula IIb to provide (2R,6R)-hydroxynorketamine if the carbamate linkage of the compound of Formula IIa was cleaved, or (2S,6S)-hydroxynorketamine if the carbamate linkage of the compound of Formula IIb was cleaved

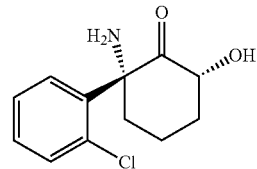

(2R,6R)-hydroxynorketamine

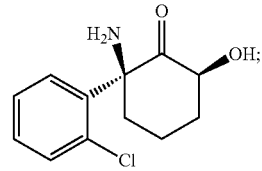

(2S,6S)-hydroxynorketamine wherein $R^1$ is $C_1$-$C_6$ alkyl, $C_1$-$C_6$ haloalkyl, benzyl, 4-methoxybenzyl, or 2-trimethylsilylethyl.

2. The method according to claim 1, wherein $R^1$ is tert-butyl and wherein cleaving the carbamate linkage comprises treatment of the compound of Formula IIa or Formula IIb with acid.

3. The method according to claim 2, wherein the acid is trifluoroacetic acid.

4. The method according to claim 1, additionally comprising treating (2R,6R)-hydroxynorketamine with hydrochloric acid to manufacture (2R,6R)-hydroxynorketamine hydrochloride salt, or treating (2S,6S)-hydroxynorketamine with hydrochloric acid to manufacture (2S,6S)-hydroxynorketamine hydrochloride salt.

5. The method according to claim 1, wherein the base is lithium diisopropylamide, sodium hexamethyldisilazane, potassium hexamethyldisilazane, or sec-butyllithium, and the compound of Formula Ia or Formula Ib is treated with the base at a temperature below 0° C.

6. The method according to claim 1 wherein treating the compound of Formula Ia or Formula Ib with a base comprises treating the compound of Formula Ia or Formula Ib with lithium diisopropylamide at a temperature below −50° C.

7. The method according to claim 1 wherein the trialkylsilylchloride is trimethylsilyl chloride, triethylsilyl chloride, tert-butyldimethylsilyl chloride, or triisopropylsilyl chloride.

8. The method according to claim 7 wherein the trialkylsilylchloride is trimethylsilyl chloride.

9. The method according to claim 1, wherein the peroxy compound is a peroxy acid or a peroxide.

10. The method according to claim 9, wherein the peroxy compound is meta-chloroperoxybenzoic acid, peroxybenzoic acid, peracetic acid, dimethyldioxirane, tert-butylhydroperoxide, or hydrogen peroxide.

11. The method according to claim 1, wherein after treatment with the peroxy compound the compound of Formula Ia or Formula Ib is treated with tetra-n-butylammonium fluoride.

12. The method according to claim 1, further comprising generating the compound of Formula Ia or Formula Ib by reacting (R)-norketamine with $(R^1O_2C)_2O$ or $R^1O_2C$-X to generate a compound of Formula Ia, or reacting (S)-norketamine with $(R^1O_2C)_2O$ or $R^1O_2C$-X to generate a compound of Formula Ib; wherein X is a halogen.

13. The method according to claim 12 wherein $R^1$ is tert-butyl, and wherein generating the compound of Formula Ia comprises reacting (R)-norketamine with (tert-butyl-$O_2C)_2O$, and generating the compound of Formula Ib comprises reacting (S)-norketamine with (tert-butyl-$O_2C)_2O$.

14. The method according to claim 1, comprising

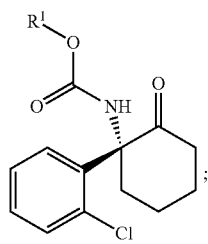

Formula Ia treating a compound of Formula Ia with lithium diisopropylamide at a temperature below −50° C., then with trimethylsilylchloride, then with meta-chloroperoxybenzoic acid, and then with tetra-n-butylammonium fluoride, to provide a compound of Formula IIa, wherein $R^1$ is tent-butyl,

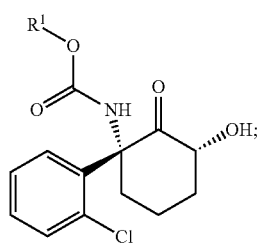

Formula IIa and cleaving the carbamate linkage in Formula IIa by treatment with acid to provide (2R,6R)-hydroxynorketamine

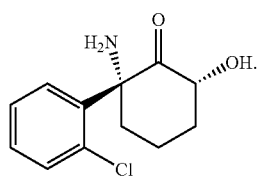

((2R,6R)-hydroxynorketamine)

15. The method according to claim 1, comprising

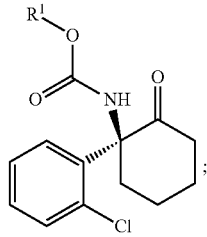

Formula Ib treating the compound of Formula Ib with lithium diisopropylamide at a temperature below −50° C., then with trimethylsilylchloride, then with meta-chloroperoxybenzoic acid, and then with tetra-n-butylammonium fluoride, to provide a compound of Formula IIb, wherein $R^1$ is tert-butyl,

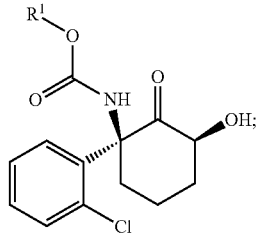

Formula IIb and cleaving the carbamate linkage in Formula IIb by treatment with acid to provide (2S,6S)-hydroxynorketamine

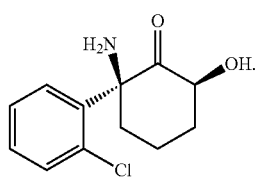

((2S,6S)-hydroxynorketamine)

\* \* \* \* \*